United States Patent
Johansen et al.

(10) Patent No.: US 10,092,701 B2
(45) Date of Patent: Oct. 9, 2018

(54) MEDICAL CARTRIDGE COMPRISING A ONE WAY VALVE

(71) Applicant: Medicom Innovation Partner A/S, Struer (DK)

(72) Inventors: Esben W. Johansen, Struer (DK); Niels Kure, Skaevinge (DK); Henrik Leisner, Jaegerspris (DK)

(73) Assignee: MEDICOM INNOVATION PARTNER A/S, Struer (DK)

(*) Notice: Subject to any disclaimer, the term of this patent is extended or adjusted under 35 U.S.C. 154(b) by 31 days.

(21) Appl. No.: 15/306,878

(22) PCT Filed: May 18, 2015

(86) PCT No.: PCT/EP2015/060874
§ 371 (c)(1),
(2) Date: Oct. 26, 2016

(87) PCT Pub. No.: WO2015/177082
PCT Pub. Date: Nov. 26, 2015

(65) Prior Publication Data
US 2017/0043094 A1    Feb. 16, 2017

(30) Foreign Application Priority Data

May 19, 2014   (DK) ................. 2014 00268

(51) Int. Cl.
*A61M 5/31* (2006.01)
*A61M 5/24* (2006.01)
(Continued)

(52) U.S. Cl.
CPC ............. *A61M 5/31* (2013.01); *A61J 1/062* (2013.01); *A61M 5/158* (2013.01); *A61M 5/24* (2013.01);
(Continued)

(58) Field of Classification Search
CPC .......... A61M 5/31; A61M 5/158; A61M 5/24; A61M 5/2448; A61M 5/2459; A61M 5/28;
(Continued)

(56) References Cited

U.S. PATENT DOCUMENTS 554,614 A * 2/1896 Beyer ........................... 604/184
1,174,745 A * 3/1916 Lilly .............................. 604/236
(Continued)

FOREIGN PATENT DOCUMENTS

GB    2503028 A   12/2013
WO   WO-9601135 A1   1/1996
(Continued)

OTHER PUBLICATIONS

International Search Report PCT/ISA/210 for International Application No. PCT/EP2015/060874 dated Sep. 25, 2015.
(Continued)

*Primary Examiner* — Manuel Mendez
(74) *Attorney, Agent, or Firm* — Harness, Dickey & Pierce PLC

(57) ABSTRACT

A medical cartridge containing multiple doses of a medical drug is disclosed. An outlet end is arranged to be connected to an injection needle for delivering the medical drug. The medical cartridge comprises a one way valve arranged in an interior part of the medical cartridge at a position near the outlet end. The one way valve allows a fluid flow from the interior of the medical cartridge towards the outlet end, but prevents a fluid flow from the outlet end towards the interior of the medical cartridge. Thereby the risk of contamination of the medical drug remaining in the cartridge is minimized.

15 Claims, 18 Drawing Sheets

(51) Int. Cl.
*A61M 5/28* (2006.01)
*A61M 5/315* (2006.01)
*A61J 1/06* (2006.01)
*A61M 5/158* (2006.01)

(52) U.S. Cl.
CPC ........ *A61M 5/2448* (2013.01); *A61M 5/2459* (2013.01); *A61M 5/28* (2013.01); *A61M 5/31596* (2013.01); *A61M 2005/3128* (2013.01)

(58) Field of Classification Search
CPC ........ A61M 5/31596; A61M 2005/3128; A61J 1/062
USPC .......................................................... 604/207
See application file for complete search history.

(56) References Cited

U.S. PATENT DOCUMENTS

| | | | | |
|---|---|---|---|---|
| 1,712,069 | A | * | 5/1929 | Cressler ................. A61M 5/24 604/237 |
| 2,665,688 | A | * | 1/1954 | Hyslop ................... A61M 5/24 604/201 |
| 4,306,554 | A | * | 12/1981 | Schwartz ............ A61M 5/2448 604/190 |
| 5,147,323 | A | | 9/1992 | Haber et al. |
| 5,478,323 | A | | 12/1995 | Westwood et al. |
| 5,531,683 | A | | 7/1996 | Kriesel et al. |
| 6,383,168 | B1 | * | 5/2002 | Landau ................... A61M 5/30 604/236 |
| 6,514,231 | B1 | | 2/2003 | Szapiro et al. |
| 7,670,314 | B2 | * | 3/2010 | Wall ........................ A61M 5/19 604/135 |
| 2001/0029355 | A1 | | 10/2001 | Szames et al. |
| 2005/0245880 | A1 | | 11/2005 | Howlett et al. |
| 2006/0100590 | A1 | | 5/2006 | Thorne et al. |
| 2006/0229562 | A1 | | 10/2006 | Marsh et al. |
| 2008/0319400 | A1 | | 12/2008 | Thorne, Jr. et al. |
| 2010/0010472 | A1 | | 1/2010 | Moore |
| 2012/0253269 | A1 | | 10/2012 | Patrick et al. |
| 2012/0265171 | A1 | | 10/2012 | Thorne, Jr. et al. |
| 2014/0052074 | A1 | | 2/2014 | Tekeste |
| 2014/0263467 | A1 | | 9/2014 | Wardle et al. |
| 2015/0144127 | A1 | | 5/2015 | Ekman et al. |

FOREIGN PATENT DOCUMENTS

| | | |
|---|---|---|
| WO | WO-02/05877 A1 | 1/2002 |
| WO | WO-2006066336 A1 | 6/2006 |
| WO | WO-2014081785 A1 | 5/2014 |

OTHER PUBLICATIONS

Written Opinion of the International Searching Authority PCT/ISA/237 for International Application No. PCT/EP2015/060874 dated Sep. 25, 2015.

International Preliminary Report on Patentability PCT/IPEA/409 for International Application No. PCT/EP2015/060874 dated May 2, 2016.

* cited by examiner

MEDICAL CARTRIDGE COMPRISING A ONE WAY VALVE

CROSS-REFERENCE TO RELATED APPLICATIONS

This application is the U.S. National Phase application of PCT Application No. PCT/EP2015/060874 filed on May 18, 2015, which claims priority to Danish Patent Application No. PA201400268 filed on May 19, 2014, the entire contents of each of which are incorporated herein by reference.

FIELD OF THE INVENTION

The present invention relates to a medical cartridge containing multiple doses of a medical drug. The medical cartridge of the invention allows the medical drug contained in the medical cartridge to be utilized to the greatest possible extent.

BACKGROUND OF THE INVENTION

Cartridges containing medical drugs may be intended for single use or for multiple uses. In the case that the cartridge is intended for single use, only one dose of medical drug is supposed to be dispensed from the cartridge, and any remaining medical drug, exceeding the required dose, is disposed of. Accordingly, the remaining medical drug is wasted. An advantage of single use cartridges is that the cartridge is sealed during filling of the cartridge, and this seal is only broken when the single dose is to be dispensed. Thereby the risk of contamination of the medical drug is minimised, and it is not necessary to add preservatives to the medical drug. However, it is a disadvantage of single use cartridges that the amount of medical drug contained in the cartridge will often not correspond precisely to a required dose, and thereby a substantial waste of medical drug may result, as described above.

On the other hand, in the case that the cartridge is intended for multiple uses, the amount of medical drug contained in the cartridge represents several doses of medical drug. This allows the total amount of medical drug contained in the cartridge to be used to a greater extent than is the case for single use cartridges, even if the required dose varies from one user to another. Accordingly, the waste of medical drug is reduced. However, once the first dose of medical drug has been dispensed from a multiple use cartridge, the sealing of the cartridge has been breached, and there is therefore a risk that the medical drug remaining in the cartridge is contaminated. In order to prevent, e.g., bacterial growth in the remaining medical drug, preservatives are sometimes added to the medical drug. However, the presence of preservatives in the medical drug may be undesirable, e.g. due to possible instability of the medical drug, undesired side effects caused by the preservatives, such as allergic reactions, etc.

In the case that the medical drug is very expensive, it is desirable to minimise the waste of the medical drug as much as possible. However, the presence of preservatives in the medical drug may be unacceptable, and therefore simply using a multiple use cartridge is not an applicable solution.

U.S. Pat. No. 5,478,323 discloses a removable manifold assembly for attachment to the outlet end of a multi-cartridge injection device. The manifold assembly comprises two rigid plastic housings which encapsulate a rubber septum. Check valves are formed by compressing the front surface of the septum against a seal face of the rear housing to form a fluid tight interface therebetween. The check valves prevent that fluid flowing from one cartridge enter one of the other cartridges.

U.S. Pat. No. 5,147,323 discloses a multiple cartridge syringe, including a body housing first and second pharmaceutical-filled cartridges. The cartridges are of the type with a septum at one end and a piston at the other end with liquid pharmaceutical between the two. When the cartridges are mounted within the body, the septums are pierced by hollow spikes which are connected to a flow path opening into an accumulator chamber. Check valves are used at the distal ends of the spikes to prevent liquid flow back into the cartridges.

DESCRIPTION OF THE INVENTION

It is an object of embodiments of the invention to provide a medical cartridge which allows the waste of medical drug to be minimised, without requiring the use of preservatives in the medical drug.

It is a further object of embodiments of the invention to provide a medical cartridge containing multiple doses of medical drug, in which the risk of contamination of the medical drug is reduced as compared to prior art medical cartridges.

According to a first aspect the invention provides a medical cartridge containing multiple doses of a medical drug, the medical cartridge having an outlet end being arranged to be connected to an injection needle for delivering the medical drug, wherein the medical cartridge comprises a one way valve arranged in an interior part of the medical cartridge at a position near the outlet end, the one way valve being arranged to allow a fluid flow from the interior of the medical cartridge towards the outlet end, and to prevent a fluid flow from the outlet end towards the interior of the medical cartridge.

The cartridge according to the first aspect of the invention contains multiple doses of a medical drug. The medical cartridge has an outlet end, where an injection needle can be connected to the cartridge, thereby allowing medical drug to be delivered from the cartridge, via the injection needle. Thus, the cartridge is of a kind which is intended for multiple uses.

Accordingly, the sealing of the cartridge is breached when the first dose of medical drug is delivered from the cartridge, thereby introducing a potential risk of contamination of the remaining medical drug in the cartridge.

The cartridge comprises a one way valve arranged in an interior part of the medical cartridge at a position near the outlet end. The one way valve is arranged to allow a fluid flow from the interior of the medical cartridge towards the outlet end, and to prevent a fluid flow from the outlet end towards the interior of the medical cartridge. Thereby medical drug can be delivered from the interior of the cartridge, through the one way valve, and via the outlet end and an injection needle connected at the outlet end. However, no reverse flow is allowed from the outlet end, through the one way valve, and into the interior of the cartridge. Thereby the risk of contamination of the remaining drug in the cartridge is considerably reduced.

Thereby, it is possible to use a multiple dose cartridge without risking that the medical drug contained in the cartridge is contaminated, and without having to apply preservatives to the medical drug. Accordingly, the medical drug contained in the cartridge can be used fully, and the waste of medical drug is minimised. This is in particular an advantage in the case that the medical drug is of a kind which is very expensive.

The one way valve could, e.g., be in the form of a simple check valve or the like. However, it could also be of a kind which must be switched between a position which allows fluid to pass the valve and a position which prevents fluid from passing the valve. This will be described further below.

It is an advantage that the one way valve is arranged in an interior part of the cartridge, because thereby the one way valve can be designed in a manner which reduces a dead volume inside the cartridge, thereby even further reducing the waste of medical drug. Furthermore, the one way valve can be positioned inside the cartridge during a filling process, where medical drug is filled into the cartridge, thereby allowing the manufacturer to control how the one way valve is positioned with respect to the cartridge. Finally, by arranging the one way valve in the interior part of the cartridge, no additional or exterior interface between the outlet end of the cartridge and the one way valve is required, and thereby the risk of leaks at such an interface is eliminated, or at least considerably reduced.

The one way valve may replace a passive septum of the medical cartridge. According to this embodiment, the one way valve is arranged inside the cartridge, immediately adjacent to the outlet end, and in immediate contact with an injection needle connected to the outlet end of the cartridge. This design may even further reduce the dead volume inside the cartridge, thereby even further reducing the waste of medical drug.

The one way valve may be a passive valve. In this case the one way valve is of a kind which automatically ensures that fluid is only allowed to pass through the valve in one direction, without an operator having to perform any active actions.

For instance, the one way valve may comprise a resilient valve member arranged to be pushed into a sealing position when a pressure difference between a pressure prevailing between the outlet end and the one way valve and a pressure prevailing inside the cartridge is lower than a predefined threshold value, and to be pushed away from the sealing position, thereby allowing medical drug to pass the one way valve, when the pressure difference is higher than the predefined threshold value. In this case the resilient valve member may be pushed towards and away from the sealing position due to resilient properties of the material of the valve member. For instance, when the resilient valve member is pushed away from the sealing position, this may be the result of a deformation of the resilient valve member.

According to this embodiment, the one way valve is controlled by means of the pressure difference across the one way valve. When the pressure prevailing inside the cartridge is high, e.g. because a movable plunger inside the cartridge is operated in order to dispense medical drug, then the one way valve is opened by pushing the resilient valve member away from the sealing position, and medical drug is allowed to pass the one way valve, thereby allowing medical drug to be dispensed from the interior of the cartridge, through the one way valve, and via the outlet end of the cartridge and the injection needle.

On the other hand, in the case that the pressure prevailing between the outlet end and the one way valve is high, then the resilient valve member is pushed firmly into the sealing position, thereby efficiently closing the one way valve and preventing a reverse flow of fluid into the cartridge. Furthermore, the higher the pressure difference across the valve, the more the resilient valve member will be pushed into the sealing position, thereby efficiently ensuring that the one way valve is closed in this situation, and that a reverse fluid flow is thereby efficiently prevented.

The threshold value could be zero, in which case the one way valve is opened as soon as the pressure prevailing inside the cartridge exceeds the pressure prevailing between the one way valve and the outlet end of the cartridge, and the one way valve is closed as soon as the pressure prevailing between the one way valve and the outlet end of the cartridge exceeds the pressure prevailing inside the cartridge.

As an alternative, the threshold value may be a non-zero value. In this case the pressure prevailing inside the cartridge must exceed the pressure prevailing between the one way valve and the outlet end of the cartridge by a certain amount, defined by the threshold value, before the one way valve is opened, and medical drug is allowed to be dispensed from the cartridge. The non-zero threshold value provides a safety margin in the sense that a small pressure difference will not cause the one way valve to open. Furthermore, it is ensured that the one way valve is kept closed when the pressure prevailing inside the cartridge is substantially equal to the pressure prevailing between the one way valve and the outlet end of the cartridge. This further reduces the risk of accidental reverse flow of fluid into the cartridge via the one way valve.

A non-zero threshold value could, e.g., be provided by means of a biasing force biasing the one way valve towards a closed position. In this case the pressure prevailing inside the cartridge must overcome this biasing force in order to cause the one way valve to open. In some cases the threshold value being applicable when opening the valve may differ from the threshold value being applicable when closing the valve. This may be referred to as mechanical hysteresis, and will further reduce the risk of accidentally opening the one way valve, while ensuring that the one way valve is appropriately closed after a dose of medical drug has been delivered.

The one way valve may comprise a duckbill valve part. A duckbill valve is a valve which defines two tapered sections made from a resilient material. The tapered sections meet along a sealing line. When the pressure prevailing between the tapered sections exceeds the pressure prevailing at the opposing sides of the tapered sections, the tapered sections are pushed away from each other, due to deformation of the tapered sections, in particular along the sealing line, thereby opening the valve. On the other hand, when the pressure prevailing at the opposing sides of the tapered sections exceeds the pressure prevailing between the tapered sections, the tapered sections are pushed towards each other, thereby ensuring that sealing is provided along the sealing line, thereby closing the valve. Accordingly, a duckbill valve is an example of a passive one way valve which is controlled by means of a pressure difference across the valve.

As an alternative, the one way valve may comprise a back flip stop element. A back flip stop element is an element, e.g. made from a resilient material, which can be pushed towards or away from a sealing position, due to a pressure difference across the back flip stop element. For instance, the back flip stop element may be arranged near an abutment element in such a manner that a higher pressure prevailing on a first side of the back flip stop element than on a second, opposite side of the back flip stop element will cause the back flip stop element to be pushed firmly against the abutment element. However, a higher pressure prevailing on the second side of the back flip stop element than on the first side of the back flip stop element will cause the back flip stop element to be moved away from the abutment element, thereby opening a flow passage between the back flip stop element and the abutment element, causing the valve to open.

The one way valve may comprise two or more back flip stop elements arranged one behind the other along a flow direction through the one way valve. In this case the pressure difference across the one way valve must be sufficient to push each of the back flip stop elements away from a sealing position in order to open the one way valve. Furthermore, the one way valve will remain closed, even if one of the back flip stop elements fails, thereby accidentally opening a fluid passage corresponding to that back flip stop element. Accordingly, the risk of an accidental reverse fluid flow into the cartridge is even further reduced.

As another alternative, the one way valve may comprise a spring biased valve element. According to this embodiment a biasing spring biases a valve element towards a closing position of the one way valve, with respect to a valve seat. Thereby the biasing force provided by the biasing spring must be overcome by the pressure difference across the one way valve in order to move the valve element away from the valve seat and open the valve, and it is ensured that the one way valve remains closed if the pressures prevailing on either side of the one way valve are substantially equal, as described above.

One example of a one way valve comprising a spring biased valve element is a tailored ball check valve. In this case the spring biased valve element is in the form of a ball arranged in contact with a compressible spring. Alternatively, the spring biased valve element may be in the form of a hollow cylinder having a compressible spring arranged inside a cavity formed in the cylinder.

As another alternative, the one way valve may comprise a resilient sleeve arranged around another part of the one way valve, the resilient sleeve being arranged to be deformed and pushed away from the other part of the one way valve due to a pressure difference across the one way valve, thereby opening the one way valve. According to this embodiment, the one way valve is similar to the kind of valve which is normally used in bicycle tubes.

According to this embodiment, a two dimensional sealing surface is defined between the resilient sleeve and another part of the one way valve. Thereby the risk of the one way valve accidentally allowing a reverse fluid flow to pass is minimised. For instance, this embodiment is particularly suitable in the case that the medical drug contained in the cartridge is in the form of a suspension, because in this case there is a risk that small particles of the suspension may get stuck in the valve. Due to the two dimensional sealing surface, such stuck particles will not result in a leak through the one way valve.

The other part of the one way valve may be a substantially solid part. In this case the one way valve may be opened by pushing the resilient sleeve away from the substantially solid part, thereby opening a flow passage between and along the resilient sleeve and the substantially solid part. As an alternative, the other part of the one way valve may be a hollow part being provided with one or more openings defined in a wall part arranged in abutment with the resilient sleeve. In this case the one way valve may be opened by pushing the resilient sleeve away from the hollow part, at the position(s) of the opening(s), thereby opening a flow passage through the opening(s), and between and along the hollow part and the resilient sleeve.

As an alternative to the passive one way valves described above, the one way valve may be an active valve. According to this embodiment, an operator will need to perform an active action in order to open the one way valve, thereby allowing medical drug to be dispensed from the cartridge. However, the one way valve may be designed in such a manner that the one way valve is automatically operated to this effect when the cartridge is operated in order to dispense a dose of medical drug. The active one way valve may, e.g., be magnetically or electrically operated, or it may be manually operated mechanical valve.

The medical cartridge may further comprise a filler material arranged in the interior part of the cartridge in a region between the one way valve and the outlet end, said filler material allowing liquid to pass through the region.

In the case that the one way valve is not arranged immediately adjacent to the outlet end of the cartridge, a dead volume will be formed in the region between the one way valve and the outlet end of the cartridge. During operation of the cartridge in order to dispense medical drug, medical drug will inevitably be trapped in this dead volume, and when a movable plunger has been pushed as far as possible inside the cartridge, and it is therefore not possible to dispense any further medical drug from the cartridge, a residual amount of medical drug, corresponding to the trapped medical drug in the dead volume, will remain in the cartridge. This medical drug is therefore wasted.

In order to minimise the waste of medical drug, it is therefore desirable to minimise the dead volume defined inside the cartridge, including the dead volume defined between the one way valve and the outlet end of the cartridge. According to this embodiment, this is obtained by arranging a filler material in the region between the one way valve and the outlet end of the cartridge. The filler material allows liquid to pass, but it also 'occupies' some of the volume of the region between the one way valve and the outlet end of the cartridge. Thereby the volume being available for trapping medical drug is reduced, i.e. the dead volume is reduced.

The filler material could, e.g., be a fibrous material, which fills out the entire region between the one way valve and the outlet end of the cartridge, but which allows liquid to pass through the material. The dead volume in the region between the one way valve and the outlet end of the cartridge will thereby be defined by the amount of liquid which can be contained in the fibrous material.

As an alternative, the filler material could be solid, while allowing liquid to pass. For instance, the filler material could be in the form of a plurality of, e.g., spherical objects, allowing liquid to pass there between, but 'occupying' a part of the volume defined between the one way valve and the outlet end of the cartridge, thereby reducing the dead volume, i.e. the volume available for trapping medical drug.

In any event, it should be ensured that the filler material allows an injection needle to enter the region between the one way valve and the outlet end of the cartridge, in such a manner that it is brought into contact with medical drug being dispensed, even if the exact position of the injection needle can not be controlled accurately.

Alternatively or additionally, the medical cartridge may further comprise a filler material arranged in a flow path extending through the one way valve, said filler material allowing liquid to pass through the flow path.

Similarly to the situation described above, a dead volume may also be defined inside the one way valve, as a consequence of various design features of the flow path through the one way valve. It is also desirable to reduce this dead volume as much as possible, in order to reduce the potential waste of medical drug to the greatest possible extent. One way of obtaining this is to arrange a filler material in the flow path extending through the one way valve. The remarks set forth above with respect to the filler material are equally applicable here.

At least a part of the one way valve may extend into a neck portion of the medical cartridge. According to this embodiment, the effective volume between the one way valve and the outlet end of the cartridge is reduced, thereby reducing the dead volume defined in this region. Accordingly, the potential waste of medical drug is thereby reduced.

The entire one way valve may be arranged in the neck portion of the medical cartridge. As an alternative, only a part of the one way valve may be arranged in the neck portion, and the remaining part of the one way valve may be arranged in a part of the cartridge extending from the neck portion towards a stopper mounted inside the cartridge.

The medical cartridge may define a total dead volume between the one way valve and the outlet end, inside the one way valve, and in a region adjacent to the one way valve and facing away from the outlet end, said total dead volume being smaller than a residual dead volume of a neck portion of the cartridge without the one way valve. According to this embodiment, the entire dead volume defined inside the cartridge is smaller than a dead volume which would be present in the case that no one way valve was arranged inside the cartridge. Thereby the presence of the one way valve inside the cartridge reduces the dead volume, thereby reducing the waste of medical drug.

There is a risk that medical drug trapped in the region between the one way valve and the outlet end of the cartridge becomes contaminated. In some applications, this will not be considered unacceptable, because the potentially contaminated medical drug only constitutes a very small part of the next dose of medical drug being dispensed from the cartridge. However, in the case that this is considered unacceptable, the medical drug may be disposed of by means of a priming shot, which flushes the volume between the one way valve and the outlet end of the cartridge immediately prior to dispensing a dose of medical drug. Also in this case, it is desirable to reduce the dead space in this region, because the medical drug being disposed of by means of the priming shot is, of course, wasted.

According to one embodiment, a biasing force may be applied to the one way valve, biasing the one way valve towards a closed position, and a force applied by a pressure prevailing inside the cartridge must, in this case, overcome the biasing force in order to cause the one way valve to open. The biasing force may, e.g., be provided by means of a biasing spring, or by means of a resilient member. This has already been described above.

The one way valve may be mounted against an inner wall of the medical cartridge via one or more sealing parts. The sealing part(s) prevent(s) fluid from bypassing the one way valve, thereby even further reducing the risk of contamination of the medical drug inside the cartridge.

The sealing part(s) may, e.g., be in the form of one or more O-rings arranged between the one way valve and the inner wall of the medical cartridge. Alternatively, any other suitable kind of sealing part could be applied. Only one sealing part could be provided, or two or more sealing parts could be provided. Providing more than one sealing part reduces the risk of leaking, since in this case, if one of the sealing parts is breached, the other(s) will ensure that sealing is maintained.

The medical cartridge may be or form part of a prefilled syringe. According to this embodiment, the cartridge is provided in a ready-to-use form, allowing a user to directly dispense the medical drug, using the prefilled syringe. In this case the prefilled syringe will be discarded after use. The prefilled syringe may be provided with or without a stacked needle.

As an alternative, the medical cartridge may be arranged to be positioned in an injection device, possibly a reusable injection device.

It should be noted that the medical cartridge could be provided with two or more one way valves arranged one behind the other in the interior part of the cartridge. This would even further reduce the risk of a reverse fluid flow into the cartridge, and thereby the risk of contamination of the medical drug contained in the cartridge.

According to a second aspect the invention provides an injection device comprising a housing accommodating a medical cartridge according to the first aspect of the invention, and a needle interface arranged to receive an injection needle in such a manner that the injection needle gains access to the interior of the medical cartridge, via the outlet end of the medical cartridge, in order to allow medical drug to be delivered from the medical cartridge, via the injection needle.

It should be noted that a person skilled in the art would readily recognise that any features described in combination with the first aspect of the invention could also be combined with the second aspect of the invention, and vice versa. The remarks set forth above are therefore equally applicable here.

The injection device may be an auto-injector, e.g. a motor driven auto-injector. As an alternative, the injection device may be manually driven.

The injection device may be arranged to reduce a pressure inside the cartridge after an injection has been performed, thereby ensuring that the one way valve is closed. This may, e.g., be obtained by slightly pulling a piston operating on a plunger of the medical cartridge in a reverse direction. When the pressure inside the cartridge is reduced, it is ensured that the pressure prevailing between the one way valve and the outlet end of the cartridge exceeds the pressure prevailing inside the cartridge, and thereby the one way valve is kept firmly closed, and a reverse fluid flow into the cartridge is prevented.

BRIEF DESCRIPTION OF THE DRAWINGS

The invention will now be described in detail with reference to the accompanying drawings in which.

DETAILED DESCRIPTION OF THE DRAWINGS

It should be understood that the detailed description and specific examples, while indicating embodiments of the invention, are given by way of illustration only, since various changes and modifications within the spirit and scope of the invention will become apparent to those skilled in the art from this detailed description.

Figures 1A, 1B:
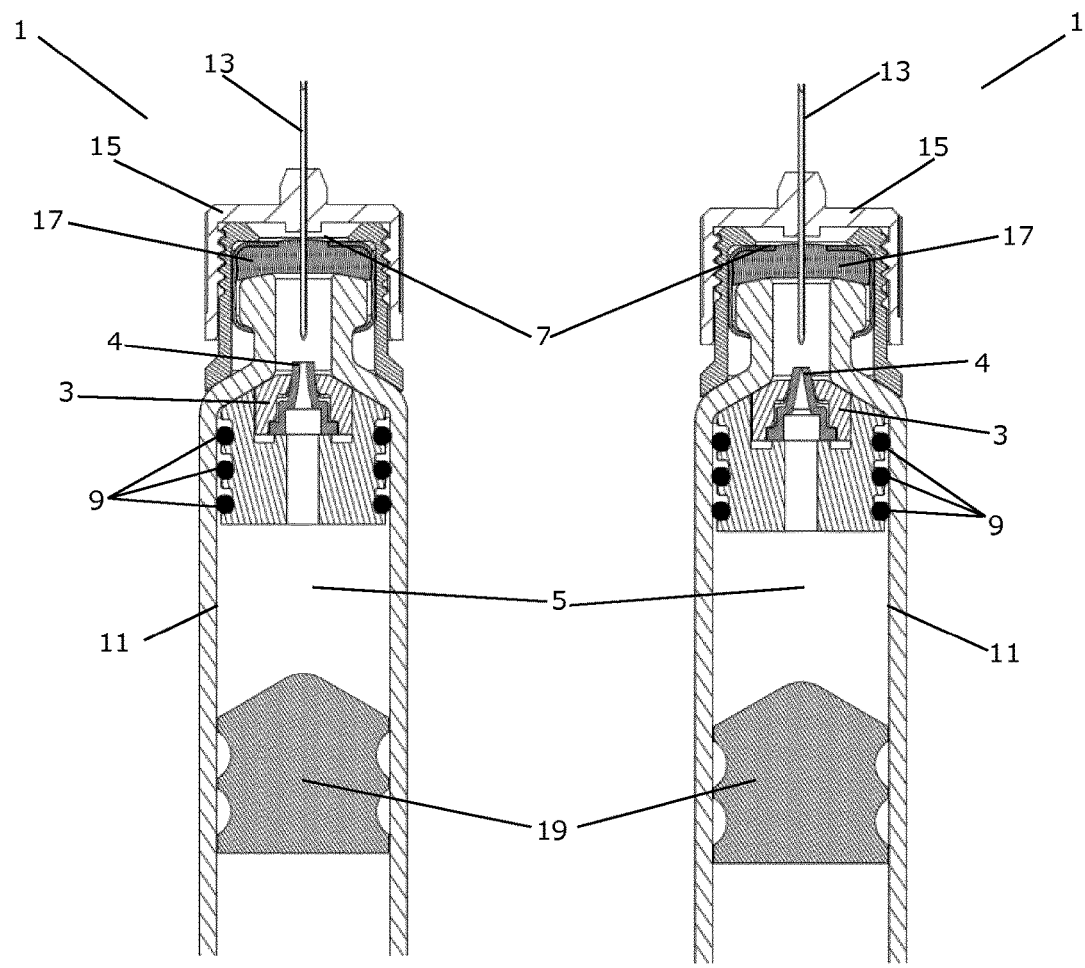
FIGS. 1-9 illustrate medical cartridges according to various embodiments of the invention.

FIGS. 1a and 1b are cross sectional views of a medical cartridge 1 according to a first embodiment of the invention. The medical cartridge 1 is provided with a one way valve 3, in the form of a duckbill valve 4, comprising two tapered sections made from a resilient material, arranged in an interior part 5 of the medical cartridge 1 at a position near an outlet end 7. The one way valve 3 is arranged to allow a fluid flow from the interior 5 of the medical cartridge 1 towards the outlet end 7, and to prevent a fluid flow from the outlet end 7 towards the interior 5 of the medical cartridge 1, in a manner which will be described below.

FIG. 1a shows the one way valve 3 in an open position, in which fluid is allowed to flow from the interior part 5 of the cartridge 1 towards the outlet end 7, and FIG. 1b shows the one way valve 3 in a closed position in which fluid is not allowed to pass the one way valve 3.

The medical cartridge 1 further comprises sealing parts 9 in the form of 3 O-rings arranged between the one way valve 3 and an inner wall 11 of the medical cartridge 1. The sealing parts 9 prevent fluid from bypassing the one way valve 3, thereby even further reducing the risk of contamination of the medical drug inside the cartridge 5.

In FIGS. 1a and 1b an injection needle 13 is mounted via a needle adapter 15 at the outlet end 7 of the cartridge 1, and extends through a septum 17.

The cartridge 1 of FIGS. 1a and 1b may be operated in the following manner. When the medical cartridge 1 is not in use, the pressure prevailing in the interior 5 of the medical cartridge 1 is equal to or lower than the pressure prevailing at the outlet end 7 of the medical cartridge 1. In this case the one way valve 3 is closed as illustrated in FIG. 1b, and fluid is not allowed to flow across the one way valve 3, whereby contamination of the drug in the interior 5 of the cartridge 1 is avoided. More specifically, the natural shape of the duckbill valve 4 is with the tapered sections of the duckbill 4 pressed together, due to the resilience of the material of the duckbill 4, thereby rendering the one way valve 3 closed, as shown in FIG. 1b.

In order to push the tapered sections of the duckbill valve 4 apart by deforming the resilient material, as shown in FIG. 1a, a force must be supplied from the interior 5 of the medical cartridge 1. This force is supplied by pressing a plunger 19 towards the one way valve 3, hereby increasing the pressure prevailing in the interior 5 of the medical cartridge 1. Thus the one way valve 3, in the form of a duckbill valve 4, is open or closed depending on the force applied to the plunger 19.

When fluid from the cartridge 1 in FIGS. 1a and 1b is to be delivered, an external force is applied to a piston (not shown) arranged in contact with the plunger 19, which in turn causes movement of the plunger 19 towards the one way valve 3. As described above, this plunger movement increases the pressure prevailing in the interior 5 of the cartridge 1, which will consequently open the one way valve 3, as shown in FIG. 1a, and allow fluid to flow across it via a path between the resilient tapered sections of the duckbill valve 4 and to be delivered via the injection needle 13.

When fluid from the cartridge 1 is no longer to be delivered, i.e. when the desired dose of medical drug has been dispensed, no external force is applied to the piston (not shown) which stops the movement of the plunger 19 towards the one way valve 3. As a consequence, the pressures prevailing in the interior 5 of the cartridge 1 and at the outlet end 7 of the cartridge 1, respectively, will equalize, which causes the resilient material of the duckbill valve 4 to return to its natural shape and closes the one way valve 3 as described above and shown in FIG. 1b. The plunger 19 may even be moved slightly in a direction away from the one way valve 3, thereby decreasing the pressure prevailing in the interior 5 of the cartridge 1. In this case the pressure prevailing at the outlet end 7 will exceed the pressure prevailing in the interior 5 of the cartridge 1. The higher pressure at the outlet end 7 will push the tapered sections of the duckbill 4 towards each other, thereby keeping the one way valve 3 firmly closed.

Since the one way valve 3 is closed, as described above, when medical drug is not being delivered from the medical cartridge 1, it is ensured that there is no reverse flow into the interior 5 of the cartridge 1, and thereby contamination of the drug remaining in the cartridge 1 after a dose of drug has been delivered, and the sealing of the cartridge 1 has therefore been broken, is efficiently prevented.

Figures 2A, 2B:
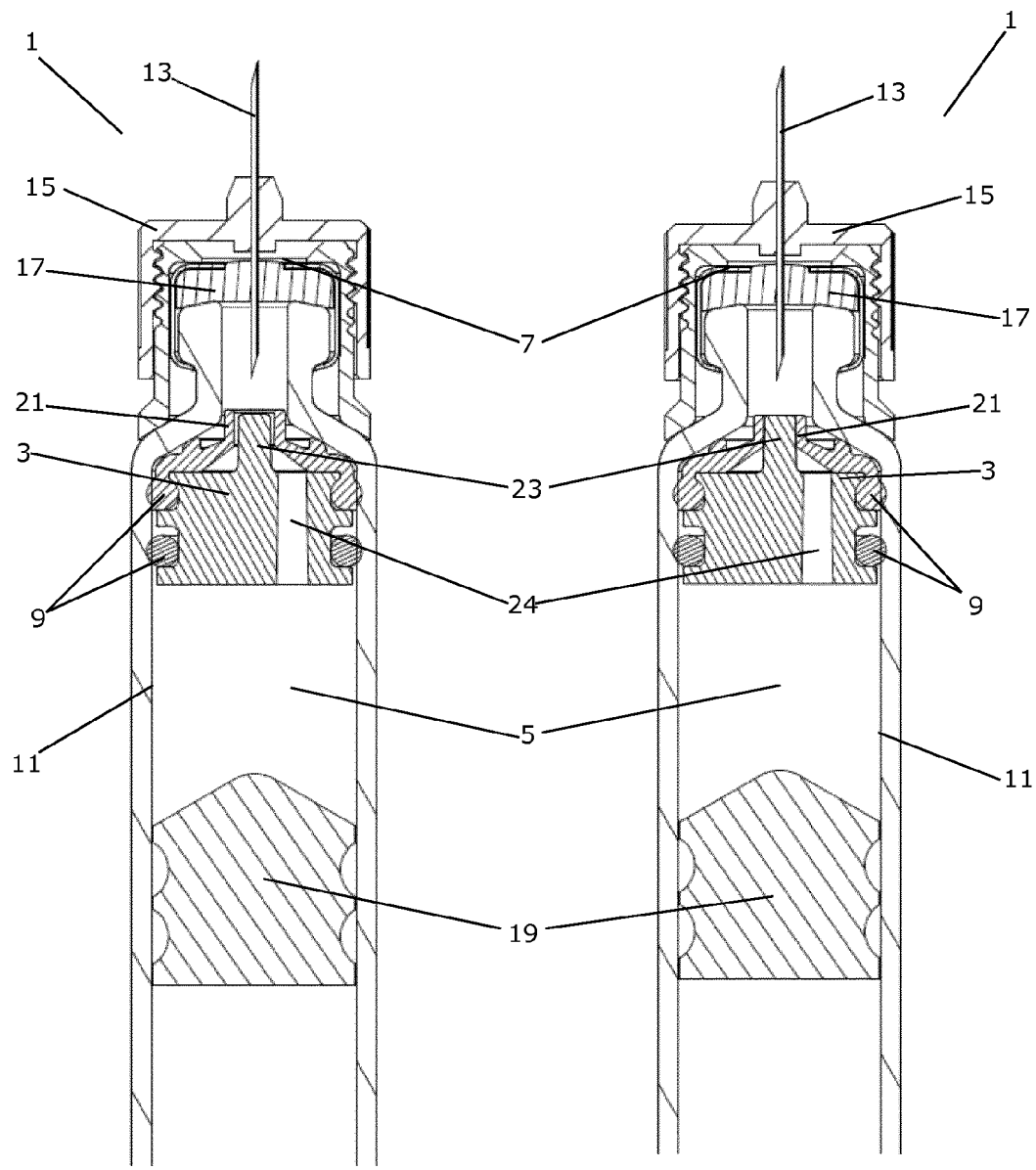

FIGS. 2a and 2b are cross sectional views of a medical cartridge 1 according to a second embodiment of the invention. The cartridge 1 in FIGS. 2a and 2b is similar to that in FIGS. 1a and 1b, and will therefore not be described in detail here. In the cartridge 1 of FIGS. 2a and 2b the one way valve 3, arranged in the interior 5 of the cartridge 1, is of a kind which comprises a resilient sleeve 21 arranged around another valve member 23, formed as a protrusion on a valve part having a number of through-going channels 24, one of which is shown, formed therein. The through-going channels 24 establish flow passages from the interior 5 of the cartridge 1 to the region accommodating the resilient sleeve 21 and the other valve member 23.

FIG. 2a shows the one way valve 3 in an open position, in which fluid is allowed to flow from the interior part 5 of the cartridge 1 towards the outlet end 7, and FIG. 2b shows the one way valve 3 in a closed position in which fluid is not allowed to pass the one way valve 3.

The medical cartridge 1 of FIGS. 2a and 2b may be operated in the following manner. When the medical cartridge 1 is not in use, the pressure prevailing in the interior 5 of the medical cartridge 1 is equal to or lower than the pressure prevailing at the outlet end 7 of the medical cartridge 1. In this case the resilient sleeve 21 assumes its natural shape and is pushed against the other valve member 23, thereby closing the one way valve 3 and preventing fluid from flowing across the one way valve 3, via a passage between the resilient sleeve 21 and the other valve member 23, as illustrated in FIG. 2b, whereby contamination of the drug in the interior 5 of the cartridge 1 is avoided.

When fluid from the cartridge 1 is to be delivered, and the pressure inside the interior 5 of the cartridge 1 is increased as a consequence of movement of the plunger 19 as described above, the resilient sleeve 21 is deformed. The deformation of the resilient sleeve 21 causes it to be pushed away from the other valve member 23, thereby allowing fluid to flow from the interior 5 via the passage which is thereby formed between the resilient sleeve 21 and the other valve member 23, to the outlet end 7 of the cartridge 1, as illustrated in FIG. 2a.

When fluid from the cartridge 1 is no longer to be delivered, the pressures prevailing in the interior 5 of the cartridge 1 and at the outlet end 7 of the cartridge 1, respectively, equalize, as described above. The resilient sleeve 21 then returns to its natural shape, and forms a seal with the other valve member 23, thereby closing the one way valve 3 as described above and shown in FIG. 2b. The plunger 19 may even be moved slightly in a direction away from the one way valve 3, thereby decreasing the pressure prevailing in the interior 5 of the cartridge 1. In this case the pressure prevailing at the outlet end 7 will exceed the pressure prevailing in the interior 5 of the cartridge 1. The higher pressure at the outlet end 7 will further push the resilient sleeve against the other valve member 23, thereby keeping the one way valve 3 firmly closed, and contamination of the drug remaining in the cartridge 1 is efficiently prevented, as described above with reference to FIGS. 1a and 1b.

The resilience of the resilient sleeve 21 may be regarded as providing a biasing force which the pressure difference across the one way valve 3 must overcome in order to push the resilient sleeve 21 away from the other valve member 23 in order to open the one way valve 3.

Figures 3A, 3B:
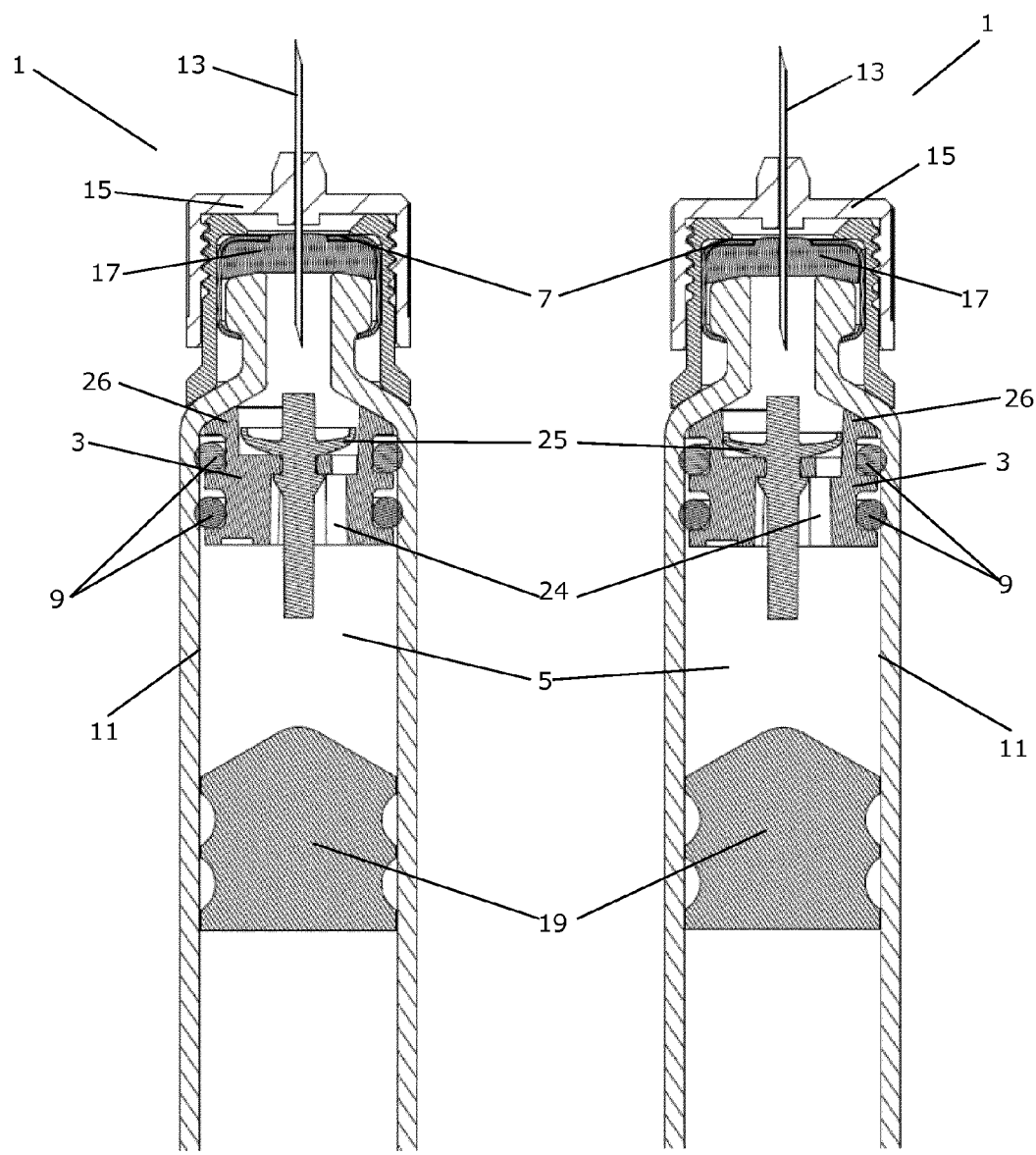

FIGS. 3a and 3b are cross sectional views of a medical cartridge 1 according to a third embodiment of the invention. The cartridge 1 in FIGS. 3a and 3b is similar to those in FIGS. 1a-2b, and will therefore not be described in detail here. In the cartridge 1 of FIGS. 3a and 3b the one way valve 3, arranged in the interior 5 of the cartridge 1 comprises a resilient valve member 25, in the form of a back flip stop element, arranged to be pushed into a sealing position pressed against a surrounding valve member 26 as its natural position.

FIG. 3a shows the one way valve in an open position, in which fluid is allowed to flow from the interior part 5 of the cartridge 1 towards the outlet end 7, and FIG. 3b shows the one way valve 3 in a closed position in which fluid is not allowed to pass the one way valve 3.

The medical cartridge 1 of FIGS. 3a and 3b may be operated in the following manner. When the medical cartridge 1 is not in use, the pressure prevailing in the interior 5 of the medical cartridge 1 is equal to or lower than the pressure prevailing at the outlet end 7 of the medical cartridge 1. In this case the resilient valve member 25 assumes its natural shape and presses against the surrounding valve member 26, thereby closing the one way valve 3 and preventing fluid from flowing across the one way valve 3 as illustrated in FIG. 3b, whereby contamination of the drug in the interior 5 of the cartridge 1 is avoided.

When fluid from the cartridge 1 is to be delivered, and the pressure inside the interior 5 of the cartridge 1 is increased as described above, due to movements of the plunger 19, the resilient valve member 25 is deformed and breaks contact with the surrounding valve member 26. This allows fluid to flow from the interior 5 of the cartridge 1, via through-going passages 24 formed in the surrounding valve member 26, and via a passage, which is thereby formed between the resilient valve member 25 and the surrounding valve member 26, to the outlet end 7 of the cartridge 1 as shown in FIG. 3a.

When fluid from the cartridge 1 is no longer to be delivered, the pressures prevailing in the interior 5 of the cartridge 1 and at the outlet end 7 of the cartridge 1, respectively, equalize, as described above. Due to the resilience of the resilient valve member 25 it will resume its natural shape, and thereby press against the surrounding valve member 26 and close the one way valve 3 as described above and shown in FIG. 3b. As described above with reference to FIG. 1, the pressure prevailing in the interior 5 of the cartridge 1 can be slightly reduced with respect to the pressure prevailing at the outlet end 7 of the cartridge 1. The higher pressure at the outlet end 7 will push the resilient valve member 25 more firmly against the surrounding valve member 26, thereby keeping the one way valve 3 firmly closed, and efficiently preventing contamination of the drug remaining in the cartridge 1, as described above with reference to FIGS. 1a and 1b.

Figures 4A, 4B:
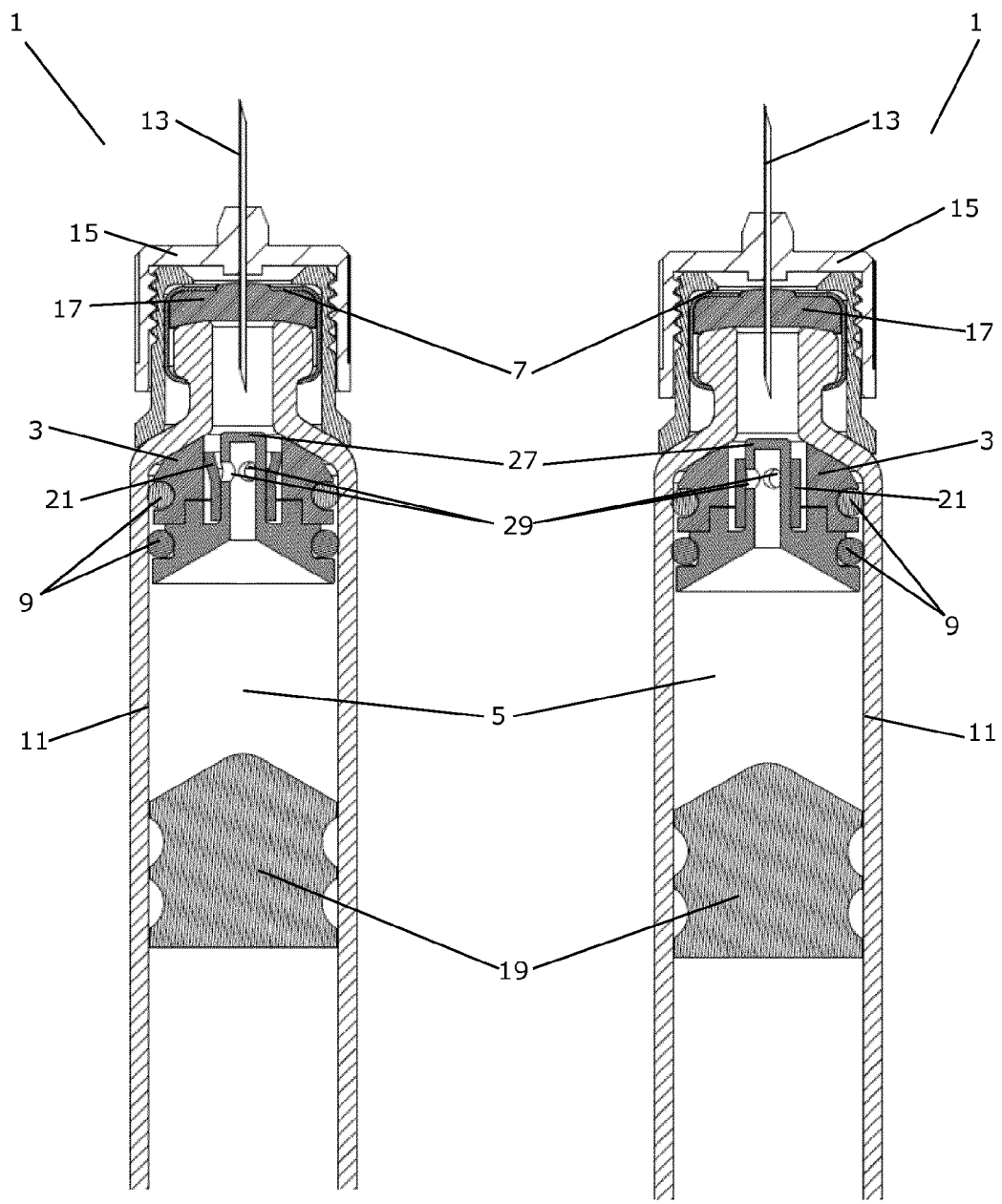

FIGS. 4a and 4b are cross sectional views of a medical cartridge 1 according to a fourth embodiment of the invention. The cartridge 1 in FIGS. 4a and 4b is similar to those in FIGS. 1a-3b, and will therefore not be described in detail here. In the cartridge 1 of FIGS. 4a and 4b the one way valve 3, arranged in the interior 5 of the cartridge 1 comprises a resilient sleeve 21 arranged around a hollow part 27 being provided with a number of openings 29 defined in a wall part thereof, which is arranged in abutment with the resilient sleeve 21.

FIG. 4a shows the one way valve 3 in an open position, in which fluid is allowed to flow from the interior part 5 of the cartridge 1 towards the outlet end 7, and FIG. 4b shows the one way valve 3 in a closed position in which fluid is not allowed to pass the one way valve 3.

The medical cartridge 1 of FIGS. 4a and 4b may be operated in the following manner. When the medical cartridge 1 is not in use, the pressure prevailing in the interior 5 of the medical cartridge 1 is equal to or lower than the pressure prevailing at the outlet end 7 of the medical cartridge 1. In this case the resilient valve sleeve 21 assumes its natural shape and is pushed into a sealing position against the hollow part 27, thereby sealing off the openings 29 in the wall part. This in turn closes the one way valve 3 and prevents fluid from flowing across the one way valve 3 as illustrated in FIG. 4b, whereby contamination of the drug in the interior 5 of the cartridge 1 is avoided.

When fluid from the cartridge 1 is to be delivered, and the pressure inside the interior 5 of the cartridge 1 is increased as described above, due to movement of the plunger 19, the resilient sleeve 21 is pushed away from the openings 29 and the hollow part 27. This allows fluid to flow from the interior 5 of the cartridge 1 via the openings 29 and along and between the wall part and the expanded resilient sleeve 21, to the outlet end 7 of the cartridge 1.

When fluid from the cartridge 1 is no longer to be delivered, the pressures prevailing in the interior 5 of the cartridge 1 and at the outlet end 7 of the cartridge 1, respectively, equalize as described above with reference to FIG. 1. Due the resilience of the resilient sleeve 21 it will resume its natural shape, and is thereby pushed into a sealing position against the hollow part 27 and closing off the openings 29, as illustrated in FIG. 4b. This closes the one way valve 3 and prevents contamination of the medical drug remaining in the interior 5 of the cartridge 1 as described above.

The pressure prevailing in the interior 5 of the cartridge 1 can be slightly reduced with respect to the pressure prevailing at the outlet end 7 of the cartridge 1, as described above with reference to FIG. 1. The higher pressure at the outlet end 7 will press the resilient sleeve 21 against the hollow part 27 and close off the openings 29 even more effectively, thereby keeping the one way valve 3 firmly closed, and efficiently preventing contamination of the drug remaining in the cartridge 1, as described above with reference to FIGS. 1a and 1b.

The resilience of the resilient sleeve 21 may be regarded as providing a biasing force which the pressure difference across the one way valve 3 must overcome in order to push the resilient sleeve away from the hollow part 27 and open the one way valve 3.

Figures 5A, 5B:
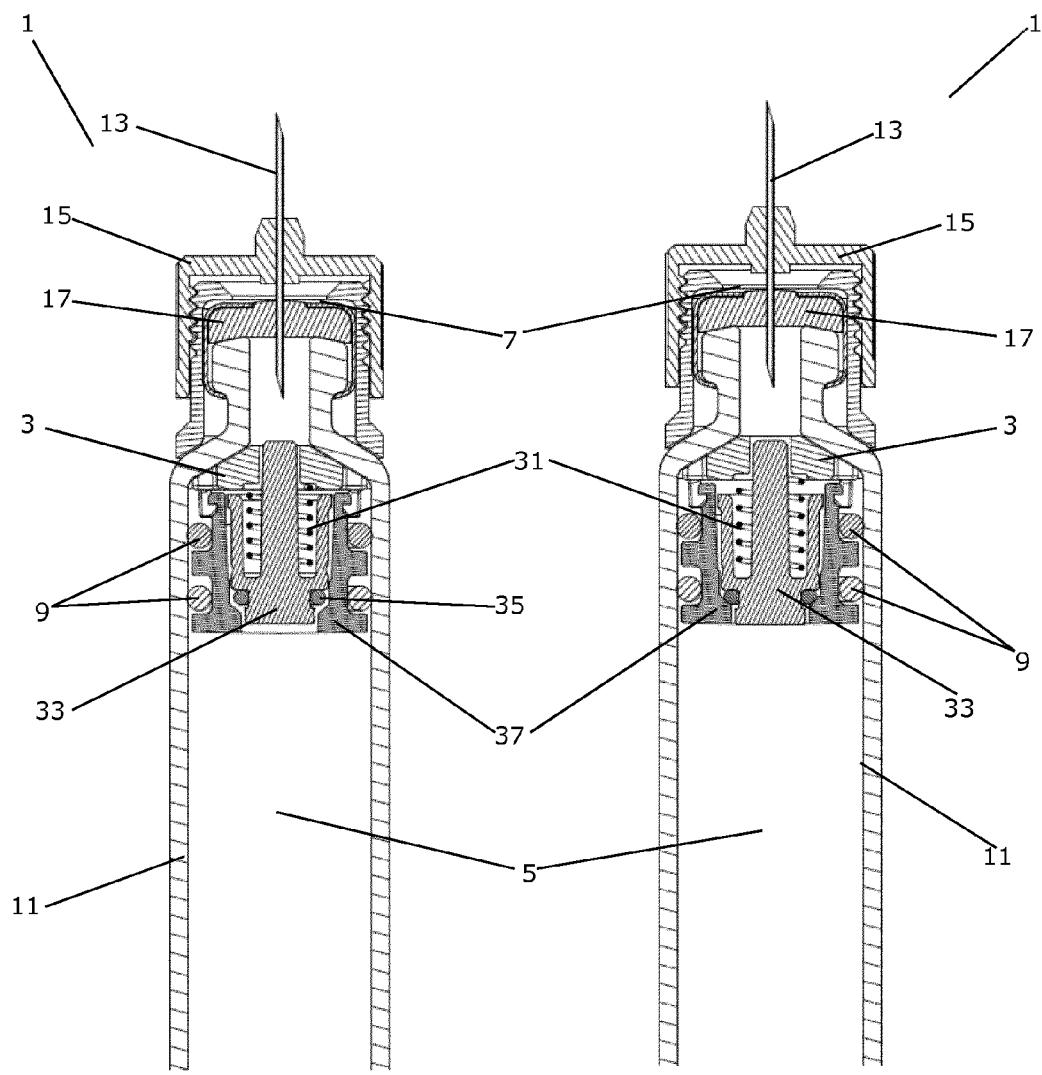

FIGS. 5a and 5b are cross sectional views of a medical cartridge 1 according to a fifth embodiment of the invention. The cartridge 1 in FIGS. 5a and 5b is similar to those in FIGS. 1a-4b, and will therefore not be described in detail here. In the cartridge 1 of FIGS. 5a and 5b the one way valve 3, arranged in the interior 5 of the cartridge 1 comprises a compressible spring 31 arranged to bias a movable valve member 33 towards a surrounding valve member 37. The movable valve member 33 is fitted with an O-ring 35 to facilitate sealing with the surrounding valve member 37 when the movable valve member 33 is arranged in contact with the surrounding valve member 37. Thus, the surrounding valve member 37 operates as a valve seat cooperating with the movable valve member 33 in order to control opening and closing of the one way valve 3.

FIG. 5a shows the one way valve 3 in in a closed position in which fluid is not allowed to pass the one way valve 3, and FIG. 5b shows the one way valve 3 in an open position, in which fluid is allowed to flow from the interior part 5 towards the outlet end 7 of the cartridge 1.

The medical cartridge 1 of FIGS. 5a and 5b may be operated in the following manner. When the medical cartridge 1 is not in use, the pressure prevailing in the interior 5 of the medical cartridge 1 is equal to or lower than the pressure prevailing at the outlet end 7 of the medical cartridge 1. In this case, a biasing force provided by the spring 31 pushes the movable valve member 33 and its fitted O-ring 35 against the surrounding valve member 37, whereby the one way valve 3 is closed as illustrated in FIG. 5a, preventing contamination of the fluid in the interior 5 of the cartridge 1 as described above with reference to FIG. 1.

As described above, the compressible spring 31 provides a biasing force, biasing the movable valve member 33 towards the surrounding valve member 37, thus biasing the one way valve 3 towards a closed position as described above. When fluid is to be delivered it requires a certain threshold pressure difference between the pressure prevailing in the interior 5 of the cartridge 1 and the pressure prevailing at the outlet end 7 of the cartridge 1, in order to push the movable valve member 33 and the O-ring 35 away from the surrounding valve member 37, and out of sealing contact, because the force applied on the movable valve member 33, due to the pressure difference, must overcome the oppositely operating biasing force applied by the compressible spring 31. Thereby the one way valve 3 remains in the closed position when the pressure prevailing in the interior 5 of the cartridge 1 is substantially equal to the pressure prevailing at the outlet end 7 of the cartridge 1. Accordingly, it is prevented that the one way valve 3 is accidentally opened, due to a slightly higher pressure in the interior 5 of the cartridge 1 than at the outlet end 7 of the cartridge 1.

When the movable valve element 33 has been moved out of sealing contact with the surrounding valve element 37, the one way valve 3 is open and fluid can flow from the interior 5 of the cartridge 1 to the outlet end 7 of the cartridge 1, through a passage that opens between the movable valve member 33, including the O-ring 35, and the surrounding valve member 37, as illustrated in FIG. 5b.

When fluid from the cartridge 1 is no longer to be delivered, the pressure prevailing in the interior 5 of the cartridge 1 is reduced. Thereby the pressure difference between the pressure prevailing in the interior 5 of the cartridge 1 and at the outlet end 7 of the cartridge 1 is reduced to a level which is smaller than the threshold pressure required to open the one way valve 3 as described. In this case, the biasing force provided by the compressible spring 31 will press the movable valve member 33, including the O-ring 35 against the surrounding valve member 37 and effectively prevent contamination of the medical drug remaining in the interior 5 of the cartridge 1 as described above.

Figures 6A, 6B:
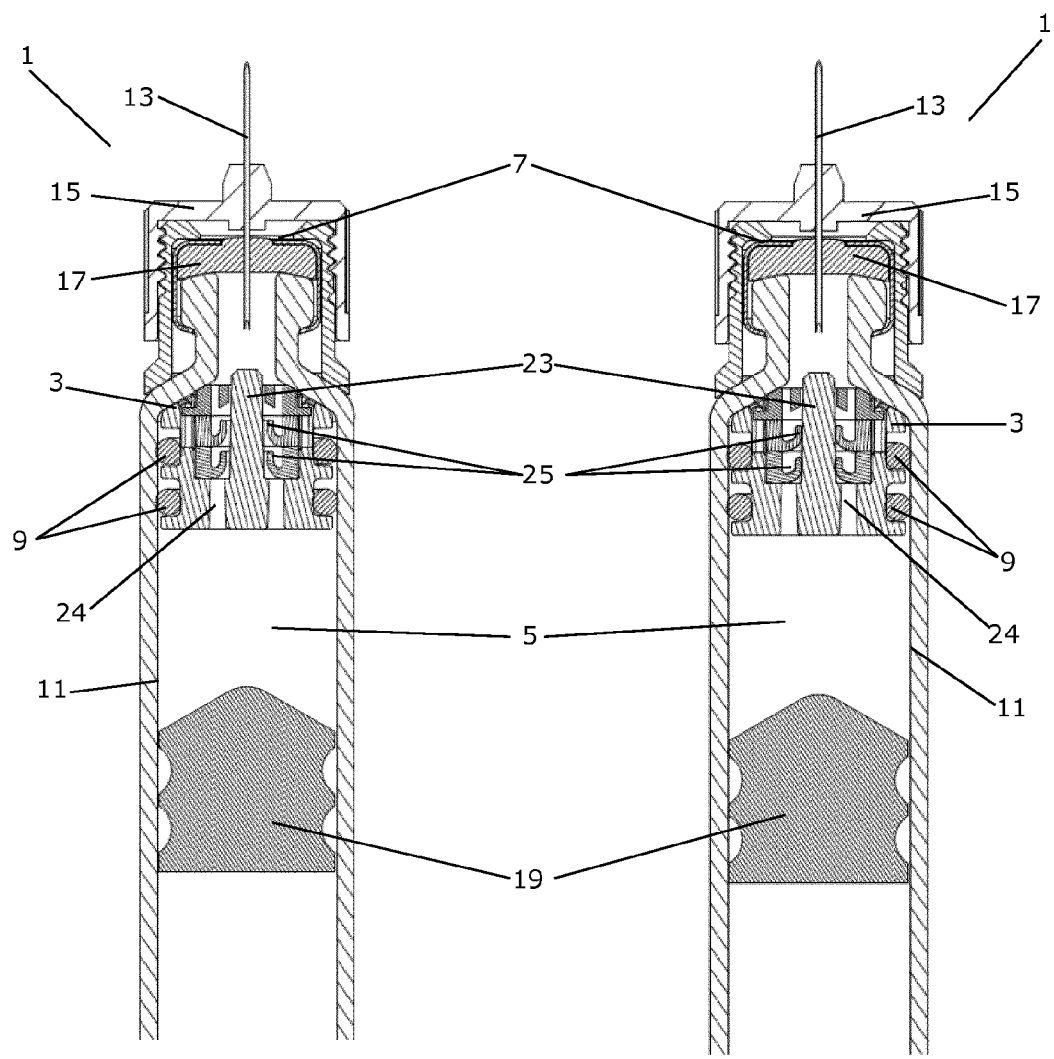

FIGS. 6a and 6b are cross sectional views of a medical cartridge 1 according to a sixth embodiment of the invention. The cartridge 1 in FIGS. 6a and 6b is similar to those in FIGS. 1a-5b, and will therefore not be described in detail here. In the cartridge 1 of FIGS. 6a and 6b the one way valve 3, arranged in the interior 5 of the cartridge 1 comprises two resilient valve members 25, in the form of back flip stop elements, placed in series, one behind the other along a longitudinal direction defined by the cartridge 1, around another valve member 23, formed as a protrusion on a valve part having a number of through-going channels 24, two of which are shown, formed therein, The through-going channels 24 establish flow passages from the interior 5 of the cartridge 1 to the region accommodating the resilient valve members 25 and the other valve member 23.

FIG. 6a shows the one way valve 3 in an open position, in which fluid is allowed to flow from the interior part 5 of the cartridge 1 towards the outlet end 7, and FIG. 6b shows the one way valve 3 in a closed position in which fluid is not allowed to pass the one way valve 3.

The medical cartridge 1 of FIGS. 6a and 6b may be operated in the following manner. When the medical cartridge 1 is not in use, the pressure prevailing in the interior 5 of the medical cartridge 1 is equal to or lower than the pressure prevailing at the outlet end 7 of the medical cartridge 1. In this case, the resilient valve members 25 are pressed against the other valve member 23, whereby the one way valve 3 is closed as illustrated in FIG. 6b preventing contamination of the fluid in the interior 5 of the cartridge 1 as described above with reference to FIG. 1.

According to this embodiment, the resilient valve members 25 have a natural position which pushes the resilient valve members 25 against the other valve member 23. When it is desired to deliver a dose of drug from the cartridge 1, the plunger 19 is moved towards the one way valve 3, thereby increasing the pressure prevailing in the interior 5 of the cartridge 1. This increased pressure causes the resilient valve members 25 to be pushed away from the other valve member 23, thereby opening a passage there between, as illustrated in FIG. 6a.

Since the cartridge 1 comprises two resilient valve members 25 arranged in series, both resilient valve members 25 must be pushed away from the other valve member 23 in order to open the one way valve 3. This reduces the risk of accidental leaks across the one way valve 3, because if a leak occurs between one of the resilient valve members 25 and the other valve member 23, the other resilient valve member 25 will ensure that the one way valve 3 remains tight. This even further reduces the risk of a reverse flow through the one way valve 3, and thereby contamination of the medical drug remaining in the interior 5 of the cartridge 1.

When fluid from the cartridge 1 is no longer to be delivered, the pressures prevailing in the interior 5 of the cartridge 1 and at the outlet end 7 of the cartridge 1, respectively, equalize, thereby closing the one way valve 3.

Figures 7A, 7B:
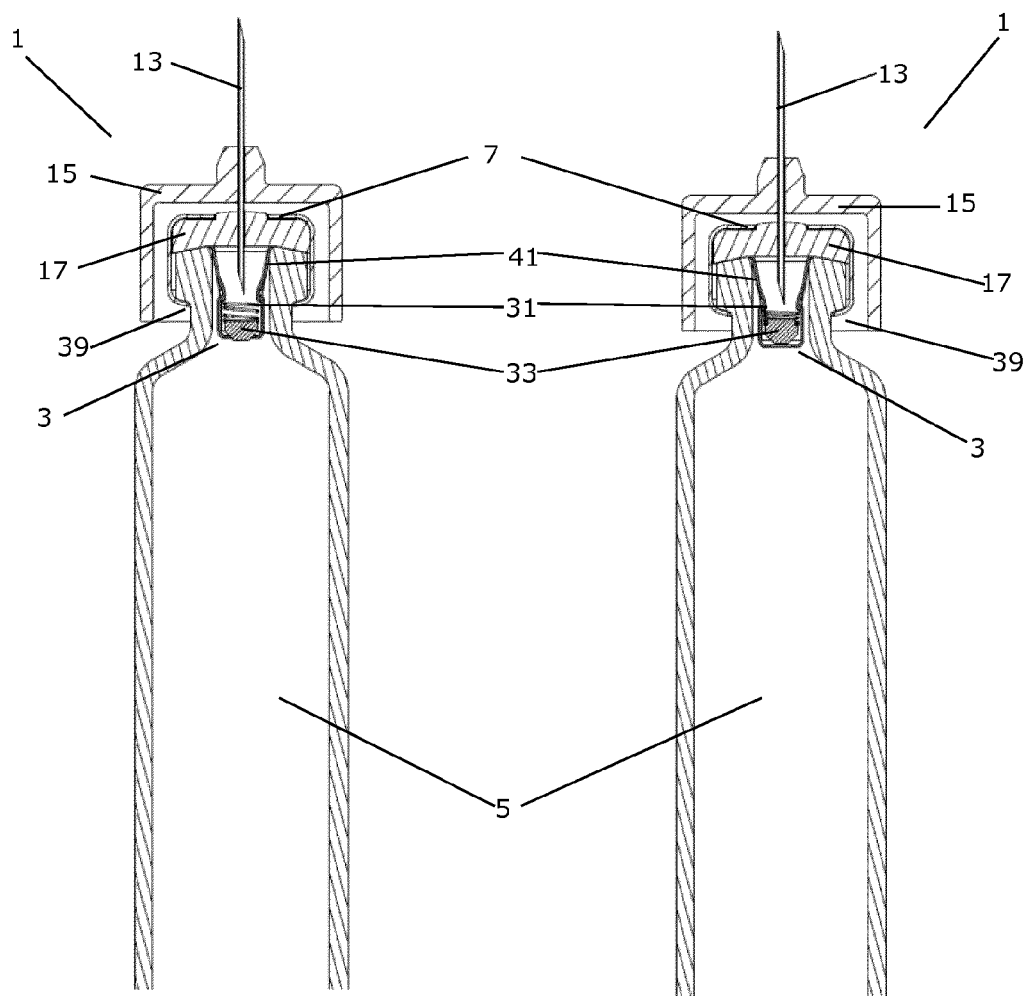

FIGS. 7a and 7b are cross sectional views of a medical cartridge 1 according to a seventh embodiment of the invention. The cartridge 1 in FIGS. 7a and 7b is similar to those in FIGS. 1a-6b, and will therefore not be described in detail here. In the cartridge 1 of FIGS. 7a and 7b the one way valve 3, arranged in the interior 5 of the cartridge 1, is arranged in a neck portion 39 of the cartridge 1. The one way valve 3 is in the form of a tailored ball check valve, comprising a compressible spring 31 arranged to bias a movable valve member 33, having a spherical shape, towards a supporting valve member 41, thereby pushing the movable valve member 33 into a sealing position.

FIG. 7a shows the one way valve 3 in in a closed position in which fluid is not allowed to pass the one way valve 3, and FIG. 7b shows the one way valve 3 in an open position, in which fluid is allowed to flow from the interior part 5 of the cartridge 1 towards the outlet end 7 of the cartridge 1.

The medical cartridge 1 of FIGS. 7a and 7b may be operated in the following manner. When the medical cartridge 1 is not in use, the pressure prevailing in the interior 5 of the medical cartridge 1 is equal to or lower than the pressure prevailing at the outlet end 7 of the medical cartridge 1. In this case, the compressible spring 31 pushes the movable valve member 33 against the supporting valve member 41, whereby the one way valve 3 is closed as illustrated in FIG. 7a preventing contamination of the fluid in the interior 5 of the cartridge 1 as described above with reference to FIG. 1. Thus, the one way valve 3 illustrated in FIGS. 7a and 7b is spring biased, and a biasing force applied on the movable valve member 33 by the compressible spring 31 must be overcome in order to open the one way valve 3. Accordingly, the pressure difference between the pressure prevailing in the interior 5 of the cartridge 1 and the pressure prevailing at the outlet end 7 of the cartridge 1 must exceed a certain threshold value before the one way valve 3 is moved from the closed position to the open position, similar to the situation described above with reference to FIGS. 5a and 5b.

The position of the one way valve 3 in the neck portion 39 of the cartridge 1 according to this embodiment reduces an effective volume defined between the one way valve 3 and the outlet end 7 of the cartridge 1, thereby reducing a dead volume defined in this region. Accordingly, the potential waste of medical drug is thereby reduced.

Figures 8A, 8B:
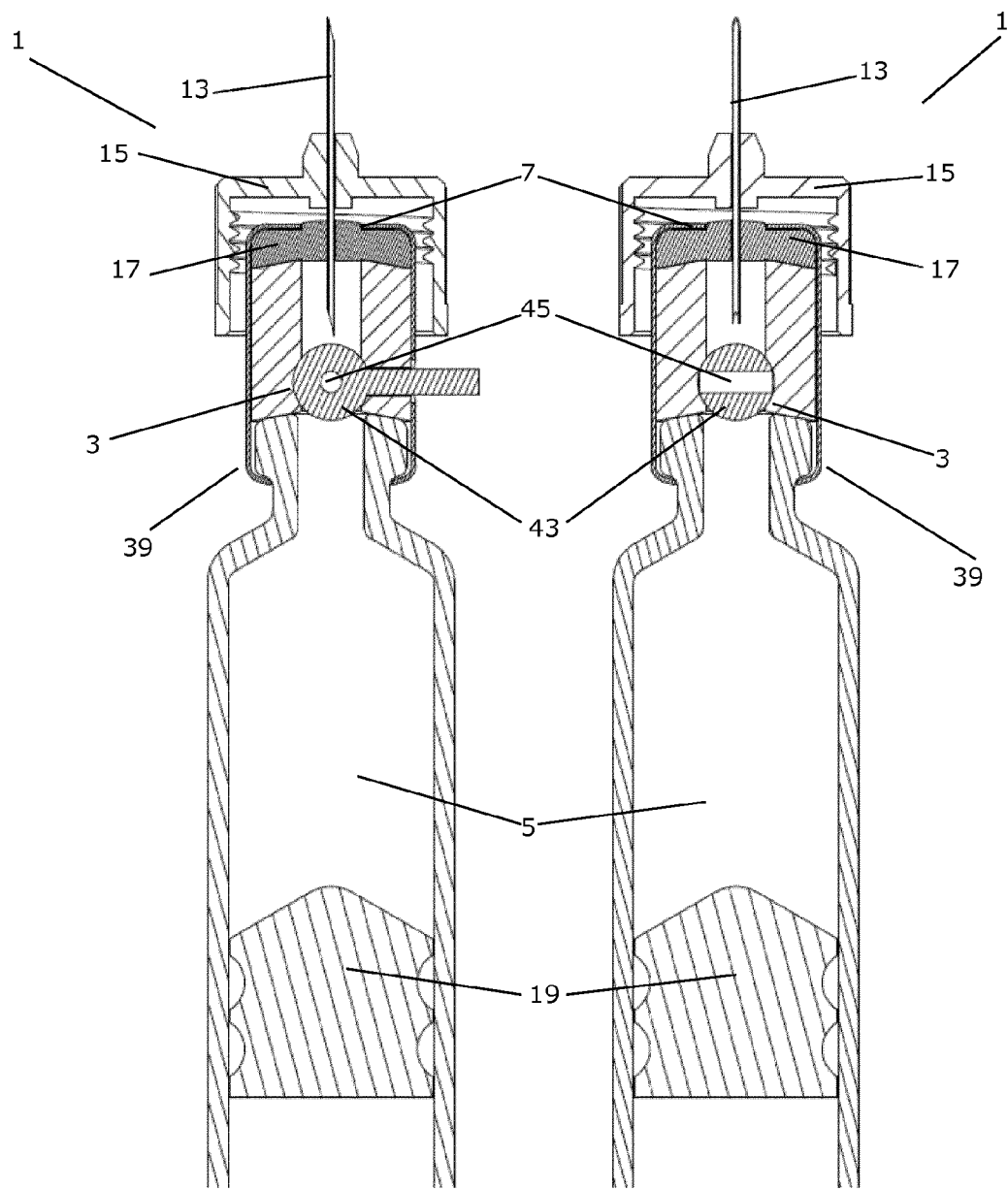
Figures 8C, 8D:
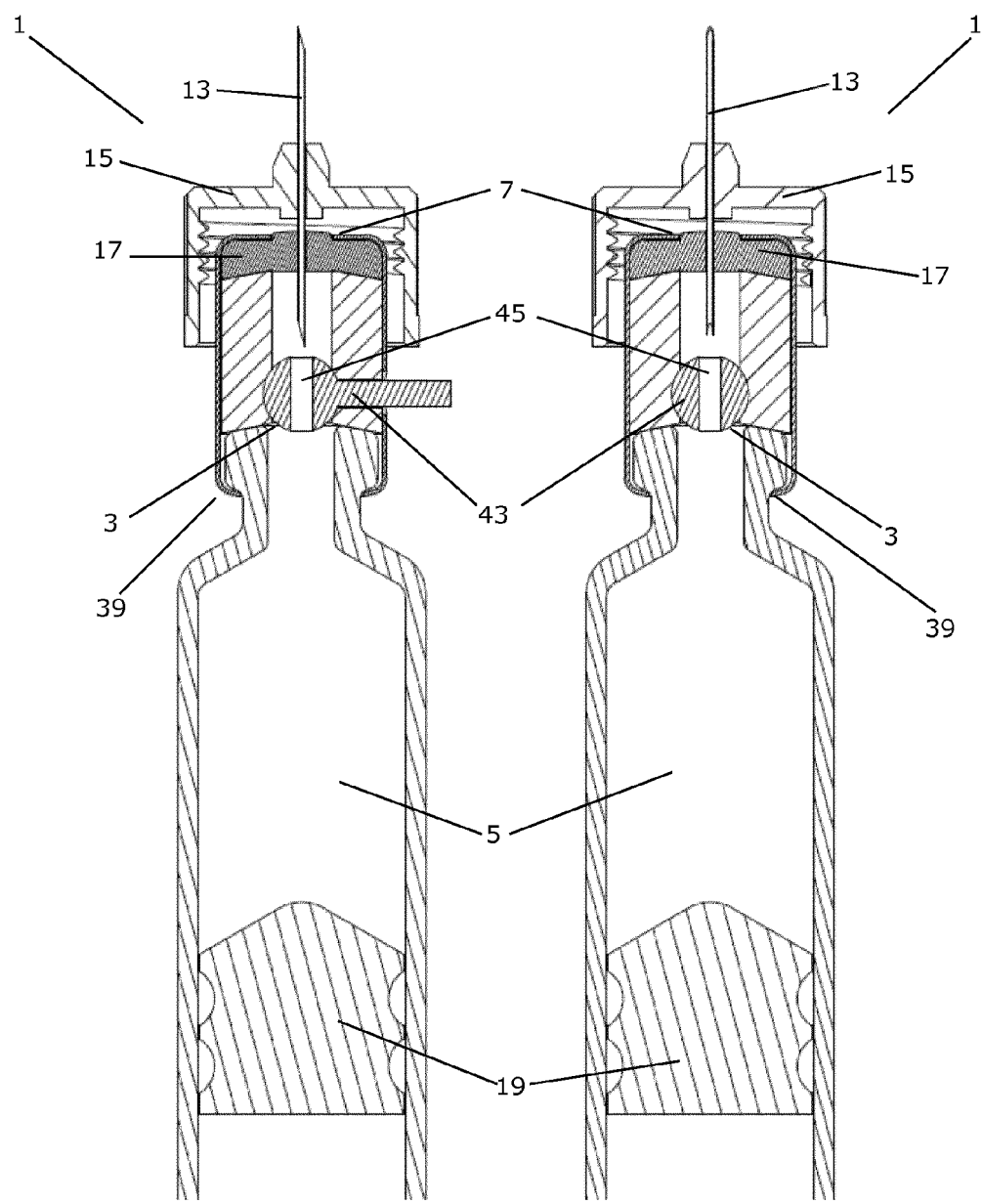

FIGS. 8a-8d are cross sectional views of a medical cartridge 1 according to an eighth embodiment of the invention. The cartridge 1 in FIGS. 8a-8d is similar to that in FIGS. 1a-7b, and will therefore not be described in detail here. FIGS. 8a and 8b show the one way valve 3 in a closed position, along two perpendicular directions, and FIGS. 8c and 8d show the one way valve 3 in an open position, along the directions defined by FIGS. 8a and 8b. In the cartridge 1, similarly to the embodiment illustrated in FIGS. 7a and 7b. The one way valve 3 is in the form of a manually operable valve part 43 with a channel 45 extending there through.

The medical cartridge 1 of FIGS. 8a-8d may be operated in the following manner. When the medical cartridge 1 is not in use, the manually operable valve part 43 is arranged in a position in which the channel 45 is oriented substantially perpendicularly to a longitudinal direction defined by the cartridge 1, i.e. substantially horizontally, as shown in FIGS. 8c and 8d. Thereby the channel 45 does not provide a fluid passage between the interior 5 of the cartridge 1 and the outlet end 7 of the cartridge 1, and a reverse fluid flow into the interior 5 of the cartridge 1 is prevented, i.e. the one way valve 3 is in a closed position, as illustrated in FIGS. 8a and 8b. Accordingly, contamination of the fluid in the interior 5 of the cartridge 1 is thereby prevented.

When fluid from the cartridge 1 is to be delivered, the manually operable valve 43 is manually rotated about an axis which is substantially perpendicular to a longitudinal direction defined by the cartridge 1, i.e. an axis which is substantially horizontal in FIGS. 8a-8d. Thereby the channel 45 is moved into a position in which it establishes a fluid passage between the interior 5 of the cartridge 1 and the outlet end 7 of the cartridge 1, i.e. the one way valve 3 is moved into an open position, as illustrated in FIGS. 8c and 8d.

When fluid from the cartridge 1 is no longer to be delivered, the manually operable valve 43 is rotated about the rotation axis defined above to the position shown in FIGS. 8a and 8b, thereby interrupting the fluid passage defined by the channel 45, and closing the one way valve 3.

It should be noted that, even though the manually operable valve part 43 illustrated in FIGS. 8a-8d is not a one way valve in a traditional sense, it is to be regarded as a one way valve in the context of the present invention, because it can be operated to allow a fluid flow from the interior 5 of the cartridge 1 towards the outlet end 7 of the cartridge 1, but prevent a fluid flow from the outlet end 7 of the cartridge 1 towards the interior 5 of the cartridge, even though this requires that the manually operable valve part 43 is actively manipulated by an operator. Accordingly, the one way valve 3 illustrated in FIGS. 8a-8d is an example of an actively operated one way valve 3. The one way valve 3 illustrated in FIGS. 8a-8d can, e.g., be moved to the closed position while the pressure prevailing in the interior 5 of the cartridge 1 is higher than the pressure prevailing at the outlet end 7 of the cartridge 1, because it is manually operated. Thereby a reverse flow into the interior 5 of the cartridge 1 can be efficiently prevented.

The position of the one way valve 3 in the neck portion 39 of the cartridge 1 according to this embodiment reduces the effective volume between the one way valve 3 and the outlet end 7 of the cartridge 1, thereby reducing the dead volume defined in this region, as described above with reference to FIGS. 7a and 7b. Accordingly, the potential waste of medical drug is thereby reduced.

Figure 9:
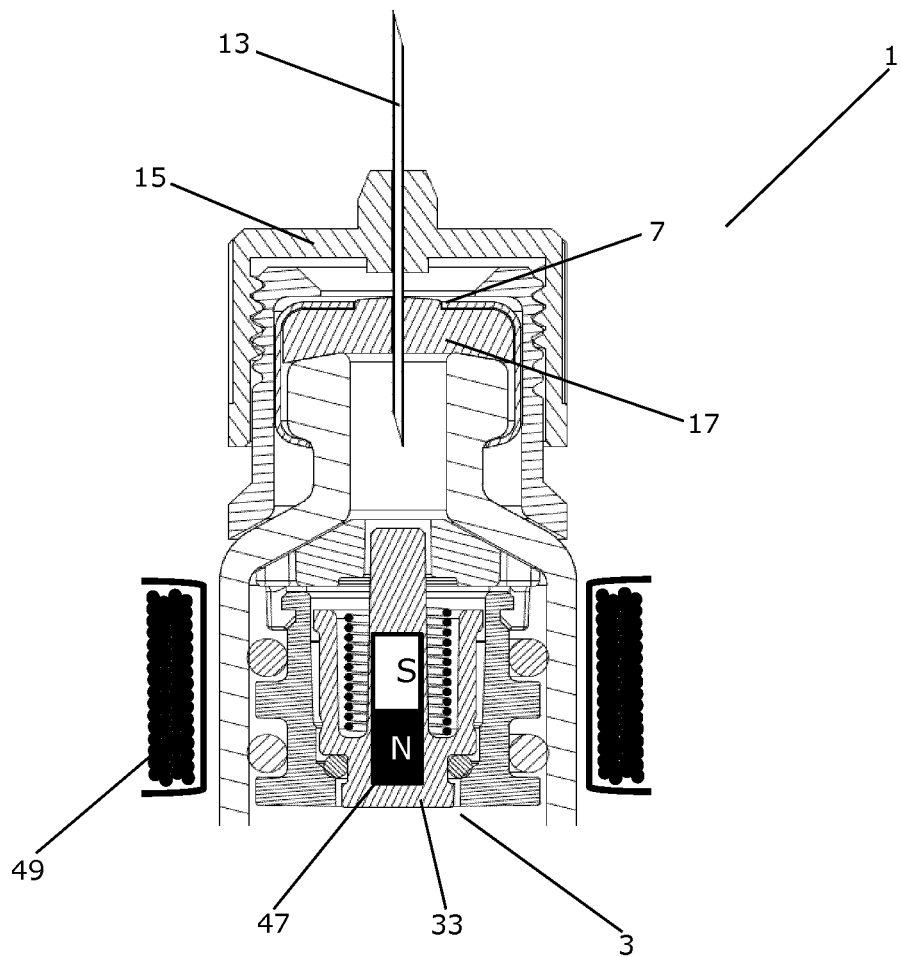

FIG. 9 is a cross sectional view of a medical cartridge 1 according to a ninth embodiment of the invention. The cartridge 1 in FIG. 9 is similar to that in FIGS. 5a and 5b, and will therefore not be described in detail here. In the cartridge 1 of FIG. 9 the one way valve 3, arranged in the interior 5 of the cartridge 1 is similar to that of the fifth embodiment in that it includes a compressible spring 31, arranged to bias a movable valve member 33 fitted with an O-ring 35 into sealing contact with a surrounding valve member 26. According to the ninth embodiment, the movable valve member 33 contains a magnetic element 47 with its north pole oriented towards the outlet end 7 and its south pole oriented towards the interior 5 of the cartridge 1. Also, the cartridge 1 is fitted with an external magnetic element 49 capable of interacting magnetically with the magnetic element 47.

FIG. 9 shows the one way valve 3 in in a closed position in which fluid is not allowed to flow from the interior part 5 towards the outlet end 7 of the cartridge 1.

The one way valve 3 in the medical cartridge 1 of FIG. 9 may be operated in a manner just like the one way valve 3 of the fifth embodiment referring to FIGS. 5a and 5b except with an added feature. Only the added feature will be described here.

When fluid is to be delivered, the external magnetic element 49 is moved in such a manner that a magnetic force forces the magnetic element 47 towards the outlet end 7 of the cartridge 1. As the magnetic element 47 is embedded in the spring loaded movable valve member 33 fitted with an O-ring 35, they all move in conjunction towards the outlet end 7 of the cartridge 1. In this case, the one way valve 3 opens, and fluid can flow from the interior 5 of the cartridge 1 to the outlet end 7 of the cartridge 1, through a passage between the movable valve member 33 with O-ring 35 and the surrounding valve member 26.

When fluid from the cartridge 1 is no longer to be delivered, the external magnetic element 49 is moved in such a manner that a magnetic force, forces the magnetic element 47 towards the interior 5 of the cartridge 1. This in turn presses the movable valve member 33 with O-ring 35 against the surrounding valve member 26, thereby closing the one way valve 3. Thus, the one way valve 3 illustrated in FIG. 9 is an example of an actively operated one way valve 3, the valve 3 being manipulated by means of magnetic forces.

The magnetic force may be provided by means of an electromagnet or by means of a permanent magnet.

A cartridge 1 fitted with a one way valve 3 according to this embodiment is particularly suited for use in an auto-injector.

Figure 10:
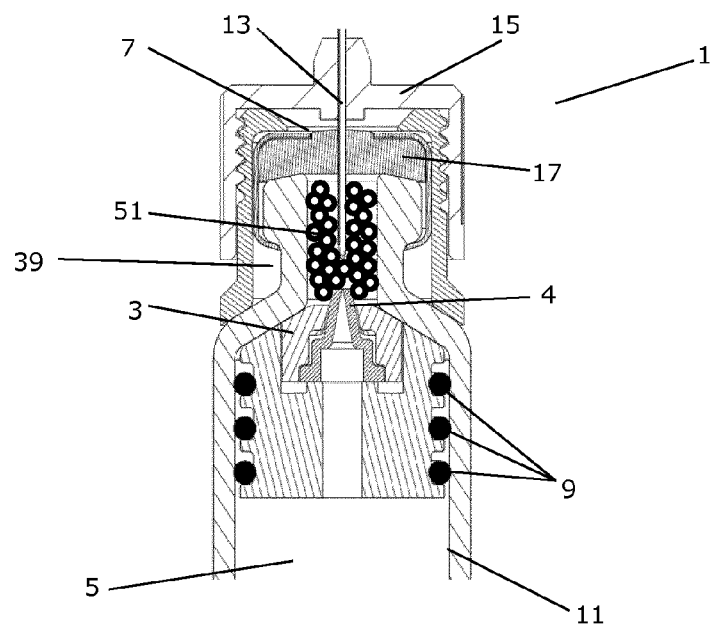
FIGS. 10-14 illustrate medical cartridges according to various embodiments of the invention, the cartridges comprising filler material.

FIG. 10 is a cross sectional view of a medical cartridge 1 according to a tenth embodiment of the invention. The cartridge 1 in FIG. 10 is similar to that in FIGS. 1a and 1b, in the sense that it comprises a one way valve 3 in the form of a duckbill valve 4.

The cartridge of FIG. 10 is provided with a filler material in the form of spheres 51 situated in the neck portion 39 of the cartridge 1, between the one way valve 3 and the outlet end 7 of the cartridge 1. Fluid is allowed to pass between the spheres 51, from the interior 5 of the cartridge 1 towards the outlet end 7 of the cartridge 1. Furthermore, the injection needle 13 is allowed to enter the region containing the spheres 51, regardless of the exact position and orientation of the injection needle 13, because the spheres 51 will simply move relative to each other, thereby allowing the injection needle 13 to enter. However, the spheres 51 'occupy' a part of the volume defined between the one way valve 3 and the outlet end 7 of the cartridge 1. This reduces the effective volume between the one way valve 3 and the outlet end 7 of the cartridge 1, thereby reducing the dead volume defined in this region. Accordingly, the potential waste of medical drug is thereby reduced.

The density, surface, shape and size of the spheres 51 may be specifically chosen so that they allow for effective operation of the one way valve 3 and allow an injection needle 13 to enter between the spheres 51.

Figure 11:
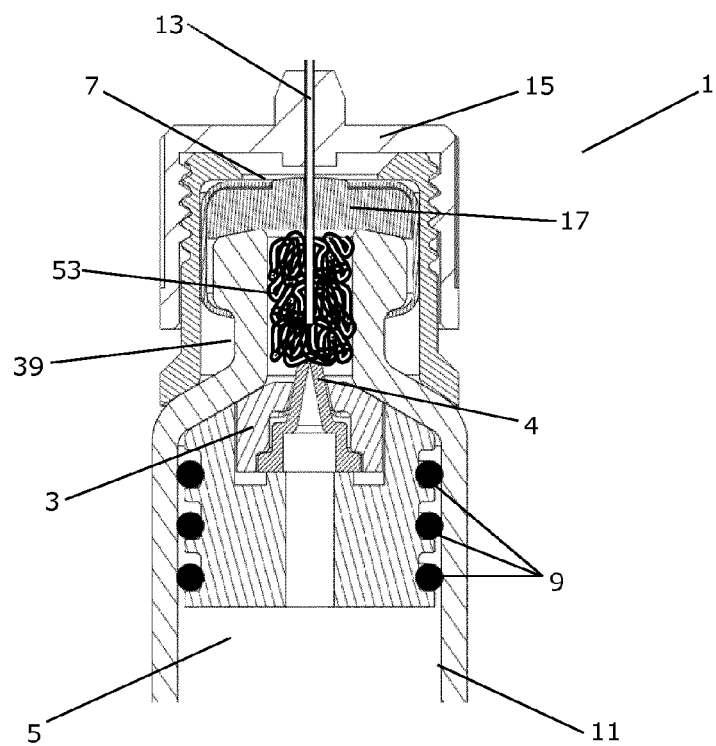

FIG. 11 is a cross sectional view of a medical cartridge 1 according to an eleventh embodiment of the invention. The cartridge 1 in FIG. 11 is similar to that in FIG. 10, in the sense that the one way valve 3 is in the form of a duckbill valve 4, and in the sense that the cartridge 1 is provided with a filler material.

The filler material shown in FIG. 11 is in the form of a fibrous material 53 situated in the neck portion 39 between the one way valve 3 and the outlet end 7 of the cartridge 1. Fluid is allowed to pass through the fibrous material 53, from the interior 5 of the cartridge 1 towards the outlet end 7 of the cartridge 1. Furthermore, an injection needle 13 is allowed to enter the region between the one way valve 3 and the outlet end 7 of the cartridge 1, due to the fibrous nature of the fibrous filler material 53. However, the presence of the fibrous material 53 reduces the effective volume between the one way valve 3 and the outlet end 7 of the cartridge 1, thereby reducing the dead volume defined in this region. Accordingly, the potential waste of medical drug is thereby reduced.

The density, rigidity and diameter of the fibres 53 may be specifically chosen so that they allow for effective operation of the one way valve 3 and allow an injection needle 13 to enter between the fibres 53.

Figure 12:
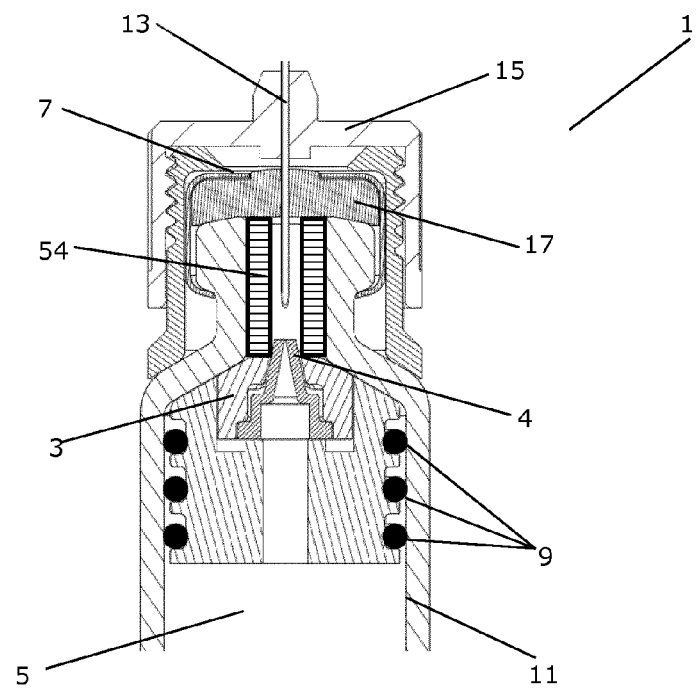

FIG. 12 is a cross sectional view of a cartridge 1 according to a twelfth embodiment of the invention. The cartridge 1 of FIG. 12 is very similar to that shown in FIGS. 1a and 1b, in the sense that it comprises a one way valve 3 in the form of a duckbill valve 4. The cartridge 1 of FIG. 12 has a filler material 54 arranged in the region between the one way valve 3 and the outlet end 7 of the cartridge 1. The filler material 54 is arranged in such a manner that no filler material 54 is arranged in a centre part of the region, thereby allowing fluid to pass through the region, via the centre part. Furthermore, an injection needle 13 can be inserted in the region without hitting the filler material 54. The presence of the filler material 54 reduces the effective volume defined in the region between the one way valve 3 and the outlet end 7 of the cartridge 1, thereby reducing the potential dead volume in this region, and reducing a potential waste of medical drug.

Figure 13:
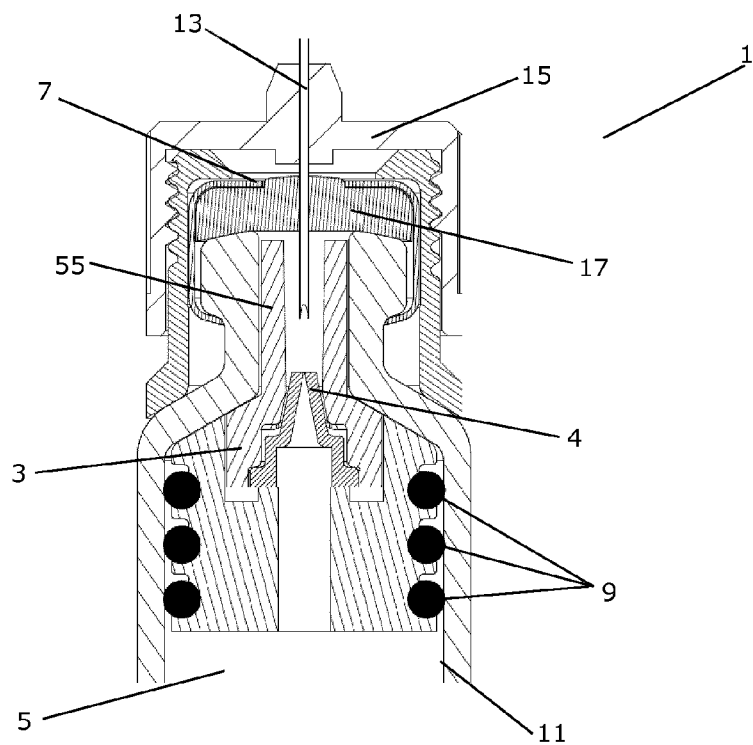

FIG. 13 is a cross sectional view of a medical cartridge according to a thirteenth embodiment of the invention. The cartridge 1 of FIG. 13 is very similar to that shown in FIGS. 1a and 1b, in the sense that it comprises a one way valve 3 in the form of a duckbill valve 4. The one way valve 3 shown in FIG. 13 has a part 55 which extends into the neck portion 39 of the cartridge 1. The part 55 which extends into the neck portion 39 is arranged in manner which is similar to the manner in which the filler material 54 is arranged in the cartridge 1 of FIG. 12. Accordingly, the part 55 which extends into the neck portion 39 reduces the effective volume in the region between the one way valve 3 and the outlet end 7 of the cartridge 1, while allowing an injection needle 13 to enter this region. Thus, the effective volume in this region is reduced, thereby reducing the potential dead volume and reducing a potential waste of medical drug.

Figure 14:
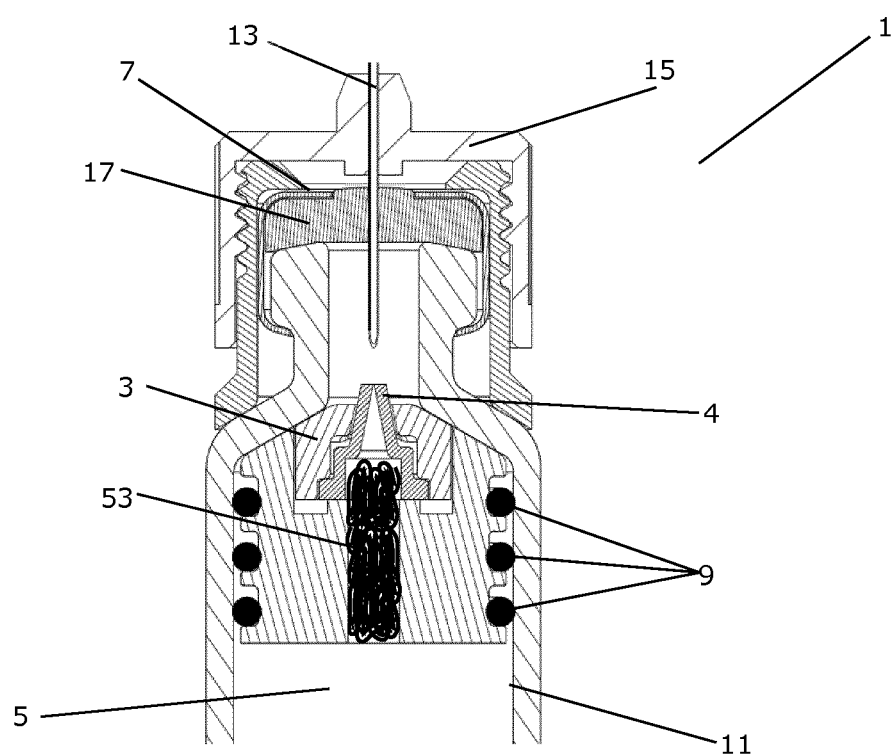

FIG. 14 is a cross sectional view of a medical cartridge 1 according to a fourteenth embodiment of the invention. The medical cartridge 1 of FIG. 14 is very similar to that shown in FIGS. 1a and 1b, in the sense that it comprises a one way valve 3 in the form of a duckbill valve 4. The cartridge 1 shown in FIG. 14 has a filler material in the form of a fibrous material 53 arranged in a flow path extending through the one way valve 3. Similarly to the situation described above with reference to FIG. 11, the fibrous material 53 allows fluid to pass through the one way valve 3, but reduces the effective volume of the flow path through the one way valve 3. Accordingly, the fibrous material 53 reduces the effective volume of the flow path, thereby reducing the dead volume in this part of the cartridge 1, and reducing a potential waste of medical drug.

Figure 15:
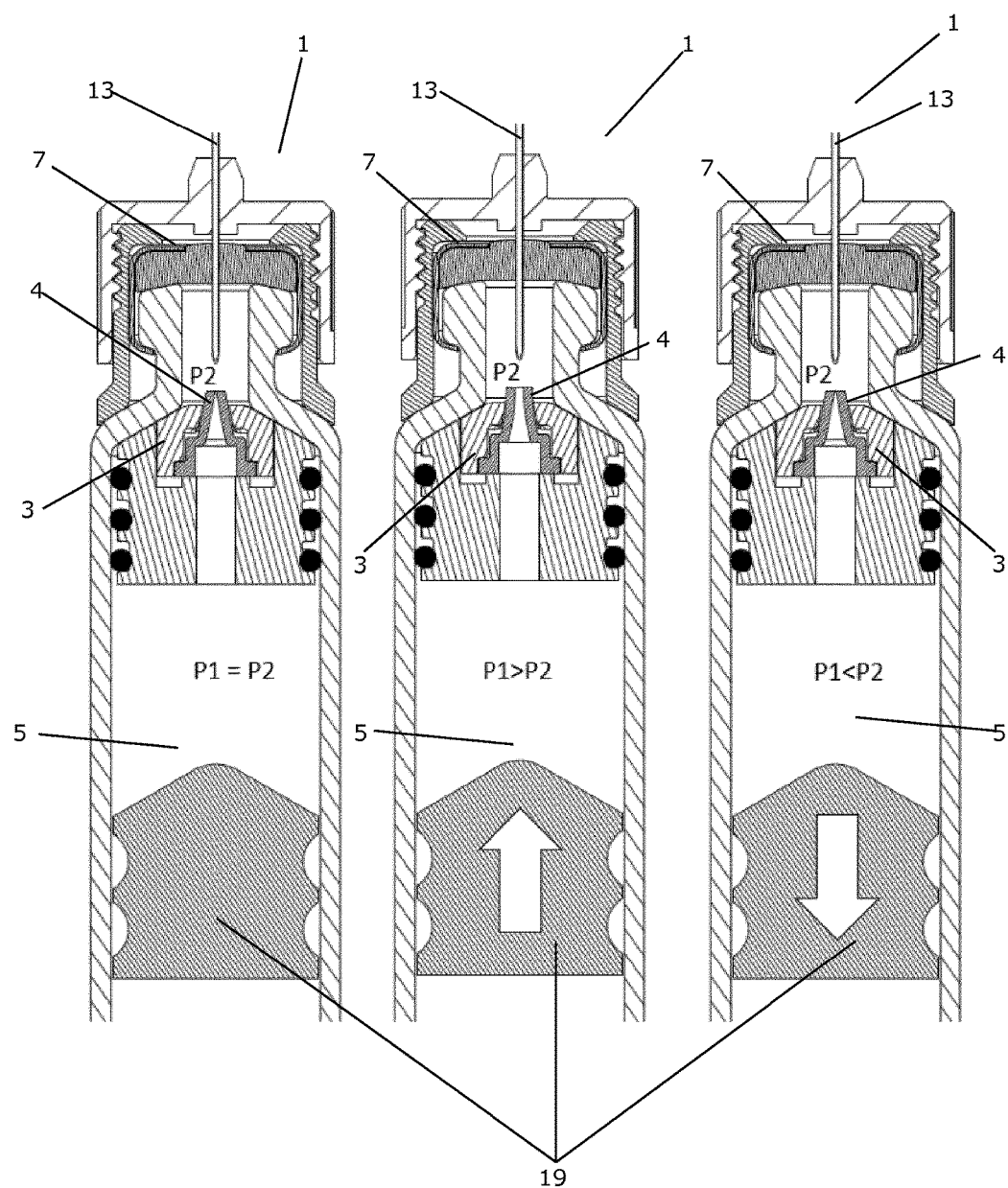
FIG. 15 illustrates plunger movement to control relative pressures in a medical cartridge according to an embodiment of the invention.

FIG. 15 shows the medical cartridge 1 of FIGS. 1a and 1b in three different situations during movement of the plunger 19. In the cartridge 1 to the left the plunger 19 is at rest. Thereby the pressure, P1, prevailing in the interior 5 of the cartridge 1 and the pressure, P2, prevailing in the region between the one way valve 3 and the outlet end 7 of the cartridge 1 are equalized, i.e. P1=P2. This causes the duckbill valve 4 to be in its natural shape, and the one way valve 3 is therefore closed, preventing a fluid flow from the outlet end 7 towards the interior 5 of the cartridge 1.

In the cartridge 1 in the middle, the plunger 19 has been moved in a direction towards the one way valve 3. This has caused an increase in the pressure, P1, prevailing in the interior 5 of the cartridge 1. Therefore the pressure, P1, prevailing in the interior 5 of the cartridge 1 exceeds the pressure, P2, prevailing in the region between the one way valve 3 and the outlet end 7 of the cartridge 1, i.e. P1>P2. This causes the tapered sections of the duckbill 4 to be deformed and moved away from each other, thereby opening the one way valve 3.

Accordingly, medical drug is allowed to pass from the interior 5 of the cartridge 1 to the outlet end 7 of the cartridge 1, via the one way valve 3.

In the cartridge 1 to the right, the plunger 19 has been moved slightly in a direction away from the one way valve 3. This has caused a decrease in the pressure, P1, prevailing in the interior 5 of the cartridge 1. Therefore the pressure, P2, prevailing in the region between the one way valve 3 and the outlet end 7 of the cartridge 1 exceeds the pressure, P1, prevailing in the interior 5 of the cartridge 1, i.e. P1<P2. The higher pressure, P2, prevailing in the region between the one way valve 3 and the outlet end 7 of the cartridge 1 pushes against the duckbill 4 in such a manner that the tapered sections of the duckbill 4 are pressed firmly against each other. Thereby it is ensured that the one way valve 3 is firmly closed, and the risk of the one way valve 3 accidentally opening is minimised.

Figure 16:
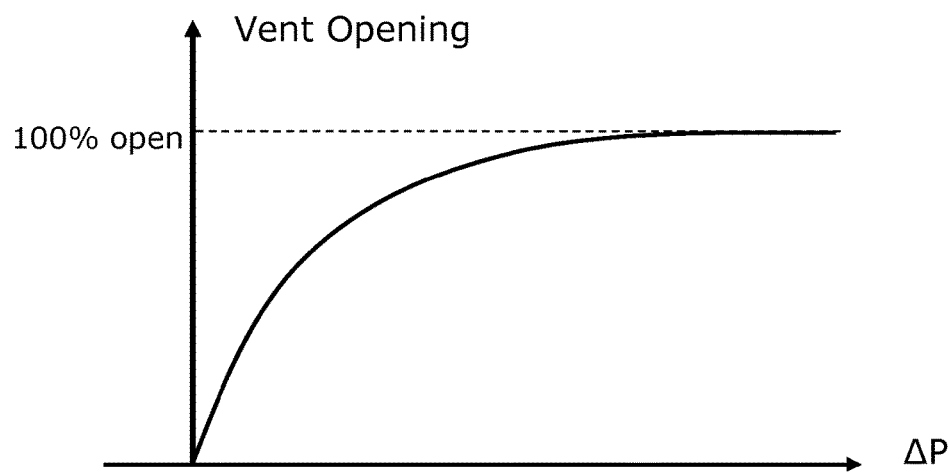
FIGS. 16-20 are graphs showing valve opening degree as a function of pressure differences for various one way valve designs.

FIG. 16 is a graph illustrating valve opening degree of a one way valve, arranged in a cartridge according to an embodiment of the invention, as a function of pressure difference, ΔP, across the one way valve. As long as the pressure difference, ΔP, across the one way valve is smaller than zero, the one way valve remains closed. As soon as the pressure difference, ΔP, is larger than zero, the one way valve starts opening, and is gradually opened, as the pressure difference, ΔP, increases, until a maximum degree is reached.

Figure 17:
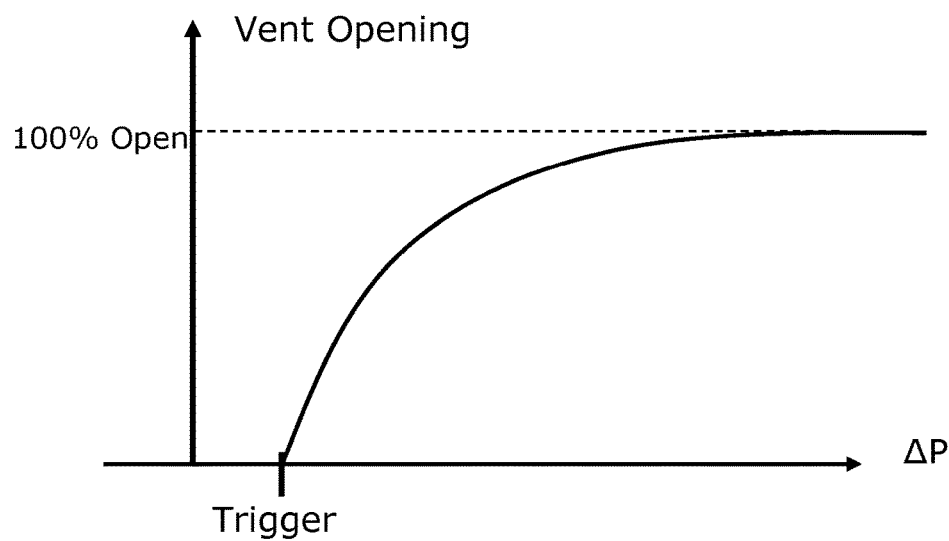

FIG. 17 is a graph illustrating valve opening degree of a one way valve, arranged in a cartridge according to an embodiment of the invention, as a function of pressure difference, ΔP, across the one way valve. The one way valve remains closed until the pressure difference, ΔP, reaches a predefined threshold value, or trigger value. Thus, in the situation illustrated in FIG. 17 the one way valve is not opened if the pressure prevailing inside the cartridge exceeds the pressure prevailing at the outlet end of the cartridge by a small amount. This reduces the risk of accidentally opening the one way valve. The threshold value may, e.g., be defined by a biasing force biasing the one way valve towards a closed position. The biasing force may, e.g., be provided by a compressible spring.

Figure 18:
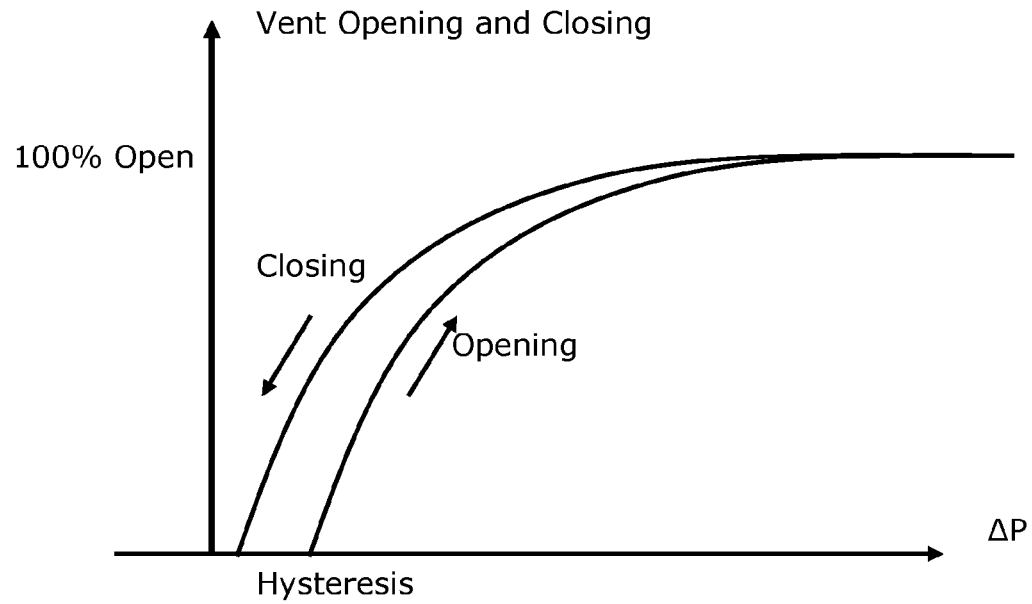
Figure 19:
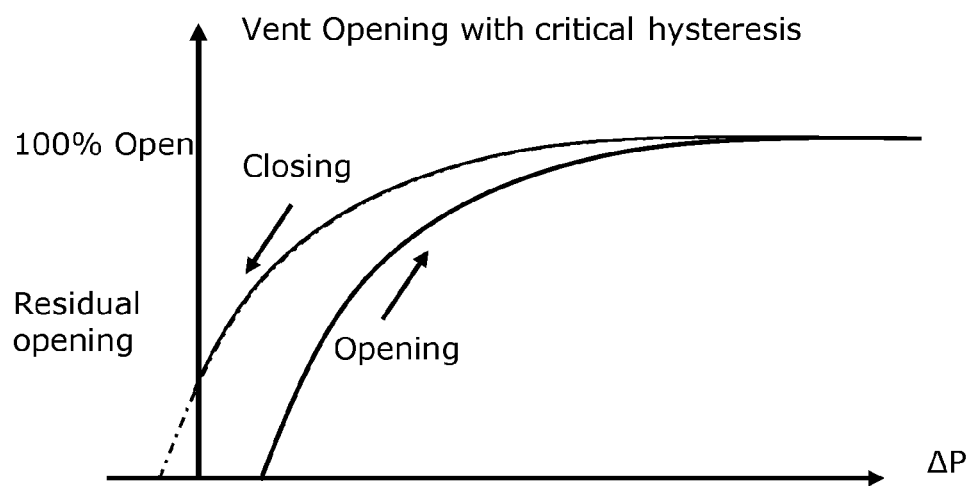
Figure 20:
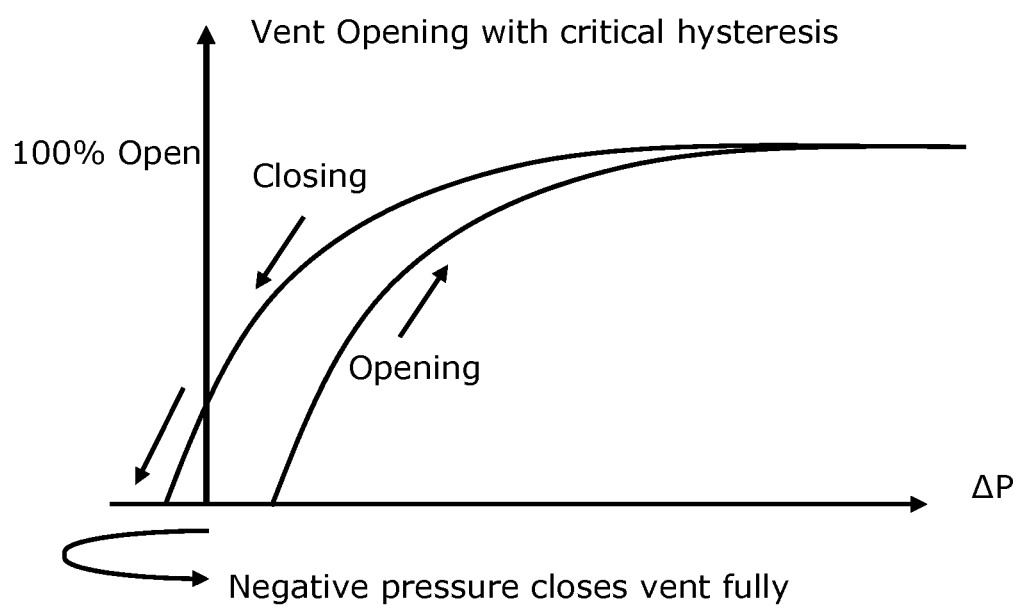

FIG. 18-20 illustrate opening degree of a one way valve as a function of pressures difference, ΔP, across the valve. In the situations illustrated in FIGS. 18-20 the opening characteristics of the valve are not identical to the closing characteristics of the valve, in the sense that a larger pressure difference, ΔP, is required in order to open the valve than in order to close the valve. This reduces the risk of accidentally opening the valve.

Figure 21:
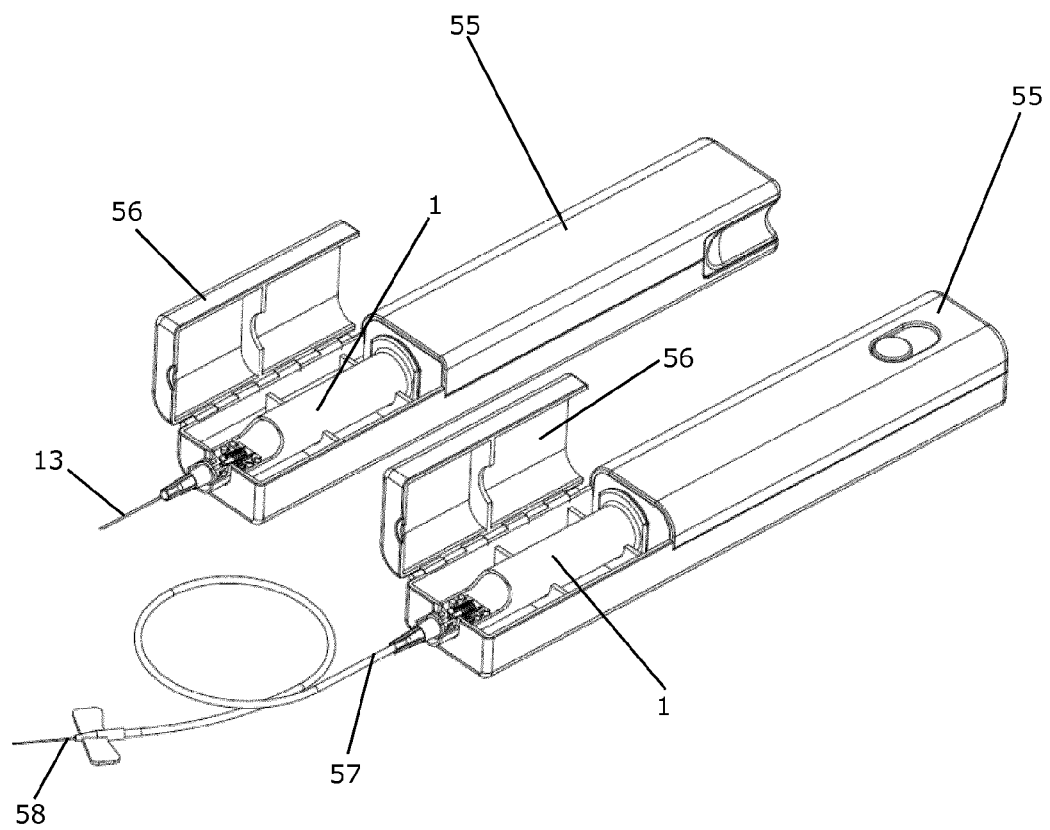
FIG. 21 illustrates an injection device containing a medical cartridge according to an embodiment of the invention.

FIG. 21 shows perspective views of an injection device 55 containing a medical cartridge 1 according to an embodiment of the invention. The medical cartridge 1 could be any of the cartridges 1 shown in FIGS. 1-14. The injection device 55 is provided with a lid 56, which can be opened in order to allow the cartridge 1 to be replaced. Thus, the injection device 55 can be reused, i.e. it can be used for delivering medical drug from a number of cartridges 1, simply be inserting a new cartridge 1 in the injection device 55 when one cartridge 1 has been emptied.

In the upper injection device 55 an injection needle 13 is mounted on the cartridge 1, thereby allowing medical drug to be directly injected from the cartridge 1, using the injection device 55. In the lower injection device 55 an infusion tube 57 is instead mounted on the cartridge 1. An infusion needle 58 is arranged at the opposite end of the infusion tube 57. Accordingly, this injection device 55 can be used for infusion purposes.

The injection device 55 comprises means (not shown) being capable of cooperating with the cartridge 1 in order to deliver a dose of drug from the cartridge 1, via the injection needle 13 or the infusion needle 58, respectively.

The invention claimed is:

1. A medical cartridge containing multiple doses of a medical drug, the medical cartridge having an outlet end being arranged to be connected to an injection needle for delivering the medical drug, wherein the medical cartridge comprises:
   a passive one way valve arranged in an interior of the medical cartridge at a position near the outlet end, the passive one way valve configured to enable a fluid flow from the interior of the medical cartridge towards the outlet end, and prevent a fluid flow from the outlet end towards the interior of the medical cartridge, the passive one way valve including a resilient valve member configured to
      be pushed into a sealing position in response to a pressure difference between a pressure prevailing between the outlet end and the passive one way valve and a pressure prevailing inside the medical cartridge being smaller than a particular threshold value, and
      be pushed away from the sealing position, thereby allowing medical drug to pass the passive one way valve, in response to the pressure difference being greater than the particular threshold value; and
   a filler material in the interior the medical cartridge in a region between the passive one way valve and the outlet end, said filler material configured to enable liquid to pass through the region between the passive one way valve and the outlet end, the filler material further configured to reduce a dead volume in the region between the passive one way valve and the outlet end to at least partially inhibit trapping of the medical drug in the region.

2. The medical cartridge according to claim 1, wherein the passive one way valve replaces a passive septum of the medical cartridge.

3. The medical cartridge according to claim 1, wherein the passive one way valve includes a duckbill valve part.

4. The medical cartridge according to claim 1, wherein the passive one way valve includes a back flip stop element.

5. The medical cartridge according to claim 1, wherein the passive one way valve includes a spring biased valve element.

6. The medical cartridge according to claim 1, wherein the passive one way valve includes a resilient sleeve arranged around another part of the passive one way valve, the resilient sleeve configured to be pushed away from the other part of the passive one way valve due to a pressure difference across the passive one way valve, thereby opening the passive one way valve.

7. The medical cartridge according to claim 1, further comprising:
   a separate filler material in a flow path extending through the passive one way valve, the separate filler material allowing liquid to pass through the flow path.

8. The medical cartridge according to claim 1, wherein the medical cartridge defines a total dead volume between the passive one way valve and the outlet end, inside the passive one way valve, and in a particular region adjacent to the passive one way valve and facing away from the outlet end, said total dead volume being smaller than a residual dead volume of a neck portion of the medical cartridge without the passive one way valve.

9. The medical cartridge according to claim 1, wherein a biasing force is applied to the passive one way valve, biasing the passive one way valve towards a closed position, and wherein a force applied by the pressure prevailing inside the medical cartridge must overcome the biasing force in order to cause the passive one way valve to open.

10. The medical cartridge according to claim 1, wherein the passive one way valve is mounted against an inner wall of the medical cartridge via one or more sealing parts.

11. The medical cartridge according to claim 1, wherein the medical cartridge is or forms part of a prefilled syringe.

12. An injection device comprising a housing accommodating the medical cartridge according to claim 1, and a needle interface arranged to receive the injection needle in such a manner that the injection needle gains access to the interior of the medical cartridge, via the outlet end of the medical cartridge, in order to allow medical drug to be delivered from the medical cartridge, via the injection needle.

13. The injection device according to claim 12, wherein the injection device is an auto-injector.

14. The injection device according to claim 12, wherein the injection device is arranged to reduce a pressure inside the medical cartridge after an injection has been performed, thereby ensuring that the passive one way valve is closed.

15. The medical cartridge according to claim 1, wherein at least a part of the passive one way valve extends into a neck portion of the medical cartridge.

\* \* \* \* \*